(12) United States Patent
Chen

(10) Patent No.: US 7,432,351 B1
(45) Date of Patent: Oct. 7, 2008

(54) B7-H1 VARIANTS

(75) Inventor: Lieping Chen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 307 days.

(21) Appl. No.: 10/679,775

(22) Filed: Oct. 6, 2003

Related U.S. Application Data

(60) Provisional application No. 60/416,203, filed on Oct. 4, 2002.

(51) Int. Cl.
*C07K 14/00* (2006.01)
*C07K 14/705* (2006.01)
*G01N 33/53* (2006.01)

(52) U.S. Cl. ........................................ 530/350; 435/7.1
(58) Field of Classification Search ........................ None
See application file for complete search history.

(56) References Cited

U.S. PATENT DOCUMENTS

| 5,580,756 | A * | 12/1996 | Linsley et al. ............... 435/69.7 |
| 7,105,328 | B2 | 9/2006 | Wood et al. |
| 2002/0102651 | A1* | 8/2002 | Freeman et al. ............ 435/69.1 |
| 2006/0153841 | A1 | 7/2006 | Freeman et al. |

FOREIGN PATENT DOCUMENTS

WO   WO 01/14556   3/2001

OTHER PUBLICATIONS

Attwood T., Science 2000; 290:471-473.*
Skolnick et al., Trends in Biotech. 2000; 18(1):34-39.*
Metzler et al., Nature Structural Biol. 1997; 4:527-531.*
Agata et al., "Expression of the PD-1 antigen on the surface of stimulated mouse T and B lymphocytes," *International Immunology*, 1996, 8:765-772.
Bajorath et al., "Molecular modeling of CD28 and three-dimensional analysis of residue conservation in the CD28/CD152 family," *J. Mol. Graph. Model.*, 1997, 15:135-139.
Berman et al., "The Protein Data Bank," *Nucl. Acids Res.*, 2000, 28:235-242.
Chambers and Allison, "Co-stimulation in T cell responses," *Curr. Opin. Immunol.*, 1997, 9:396-404.
Chapoval et al., "B7-H3: A costimulatory molecule for T cell activation and IFN-γ production," *Nature Immunology*, 2001, 2:269-274.
Connolly, "Analytical Molecular Surface Calculation," *J. Appl. Cryst.*, 1983, 16:548-558.
Cristiano and Roth, "Molecular conjugates: a targeted gene delivery vector for molecular medicine," *J. Mol. Med.*, 1995, 73:479-486.
Dong et al., "Tumor-associated B7-H1 promotes T-cell apoptosis: A potential mechanism of immune evasion," *Nature Medicine*, 2002, 8:793-800.
Dong et al., "B7-H1, a third member of the B7 family, co-stimulates T-cell proliferation and interleukin-10 secretion," *Nature Med.*, 1999, 5:1365-1369.

Engh and Huber, "Accurate Bond and Angle Parameters for X-Ray Protein Structure Refinement," *Acta Cryst.*, 1991, A47:392-400.
Fechteler et al., "Prediction of Protein Three-dimensional Structures in Insertion and Deletion Regions: A Procedure for Searching Data Bases of Representative Protein Fragments Using Geometric Scoring Criteria," *J. Mol. Biol.*, 1995, 253:114-131.
Freeman et al., "Engagement of the PD-1 Immunoinhibitory Receptor by a Novel B7 Family Member Leads to Negative Regulation of Lymphocyte Activation," *J. Exp. Med.*, 192:1027-1034.
Guatelli et al., "Isothermal, in vitro amplification of nucleic acids by a multienzyme reaction modeled after retroviral replication," *Proc. Natl. Acad. Sci. USA*, 1990, 87:1874-1878.
Hyrup et al., "Peptide Nucleic Acids (PNA): Synthesis, Properties and Potential Applications," *Bioorgan. Med. Chem.*, 1996, 4:5-23.
Ikemizu et al., "Structure and Dimerization of a Soluble Form of B7-1," *Immunity*, 2000, 12:51-60.
Ishida et al., "Induced expression of PD-1, a novel member of the immunoglobulin gene superfamily, upon programmed cell death," *EMBO J.*, 1992, 11:3887-3895.
Ishida et al., "Differential expression of PD-L1 and PD-L2, ligands for an inhibitory receptor PD-1, in the cells of lymphohematopoietic tissues," *Immunology Letters*, 2002, 84:57-62.
Krummel and Allison, "CTLA-4 Engagement Inhibits IL-2 Accumulation and Cell Cycle Progression upon Activation or Resting T Cells," *J. Exp. Med.*, 1996, 183:2533-2540.
Latchman et al., "PD-L2 is a second ligand for PD-1 and inhibits T cell activation," *Nature Immunology*, 2001, 2:261-268.
Lenschow et al., "CD28/B7 System of T Cell Costimulation," *Annu. Rev. Immunol.*, 1996, 14:233-258.
Levitt, "Accurate Modeling of Protein Conformation by Automatic Segment Matching," *J. Mol. Biol.*, 1992, 226:507-533.
Lewis, "PCR's Competitors Are Alive and Well and Moving Rapidly Towards Commercialization," *Genetic Engineering News*, 1992, vol. 12, 3 pages.
Nishimura et al., "Development of Lupus-like Autoimmune Diseases by Disruption of the PD-1 Gene Encoding an ITIM Motif-Carrying Immunoreceptor," *Immunity*, 1999, 11:141-151.
Nishimura et al., "Immunological studies on PD-1-deficient mice: implication of PD-1 as a negative regulator for B cell responses," *International Immunology*, 1998, 10:1563-1572.
Nishimura et al., "Autoimmune Dilated Cardiomyopathy in PD-1 Receptor-Deficient Mice," *Science*, 2001, 291:319-322.
Ostrov et al., "Structure of Murine CTLA-4 and Its Role in Modulating T Cell Responsiveness," *Science*, 2000, 290:816-819.
Penix et al., "Two Essential Regulatory Elements in the Human Interferon γ Promoter Confer Activation Specific Expression in T Cells," *J. Exp. Med.*, 1993, 178:1483-1496.

(Continued)

Primary Examiner—Ilia Ouspenski
(74) Attorney, Agent, or Firm—Millen, White, Zelano, Branigan, P.C.

(57) ABSTRACT

Variant costimulatory polypeptides, nucleic acids encoding such polypeptides, and methods for using the polypeptides and nucleic acids to enhance a T cell response are provided herein.

27 Claims, 12 Drawing Sheets

OTHER PUBLICATIONS

Ponder et al., "Tertiary Templates for Proteins—Use of Packing Criteria in the Enumeration of Allowed Sequences for Different Structural Classes," *J. Mol. Biol.*, 1987, 193:775-791.

Rathmell and Thompson, "The Central Effectors of Cell Death in the Immune System," *Annu. Rev. Immunol.*, 1999, 17:781-828.

Schwartz et al., "Structural mechanisms of costimulation," *Nature Immunology*, 2002, 3:427-434.

Schwartz et al., "Structural basis for co-stimulation by the human CTLA-4/B7-2 complex," *Nature*, 2001, 410:604-608.

Stamper et al., "Crystal structure of the B7-1/CTLA-4 complex that inhibits human immune responses," *Nature*, 2001, 410:608-611.

Summerton and Weller, "Morpholino Antisense Oligomers: Design, Preparation and Properties," *Antisense Nucleic Acid Drug Dev.*, 1997, 7:187-195.

Swallow et al., "B7h, a Novel Costimulatory Homolog of B7.1 and B7.2, Is Induced by TNFα," *Immunity*, 1999, 1:423-432.

Tamura et al., "B7-H1 costimulation preferentially enhances CD28-indepenent T-helper cell function," *Blood*, 2001, 97:1809-1816.

Thompson et al., "cis-Acting Sequences Required for Inducible Interleukin-2 Enhancer Function Bind a Novel Ets-Related Protein, Elf-1," *Mol. Cell. Biol.*, 1992, 12:1043-1053.

Todd et al., "Transcription of the Interleukin 4 Gene Is Regulated by Multiple Promoter Elements," *J. Exp. Med.*, 1993, 177:1663-1674.

Tseng et al., "B7-DC, a New Dendritic Cell Molecule with Potent Costimulatory Properties for T Cells," *J. Exp. Med.*, 2001, 193:839-845.

Walunas et al., "CTLA-4 Ligation Blocks CD28-dependent T Cell Activation," *J. Exp. Med.*, 1996, 183:2541-2550.

Wang et al., "Ligand Binding Sites of Inducible Costimulator and High Avidity Mutants with Improved Function," *J. Exp. Med.*, 2002, 195:1033-1041.

Wang et al., "Costimulation of T cells by B7-H2, a B7-like molecule that binds ICOS," *Blood*, 2000, 96:2808-2813.

Weiss, "Hot Prospect for New Gene Amplifier: Ligase chain reaction, a combination DNA amplifier and genetic screen could do for DNA diagnostics what PCR has done for basic molecular biology," *Science*, 1991, 254:1292-1293.

Williams and Barclay, "The Immunoglobulin Superfamily—Domains for Cell Surface Recognition," *Ann. Rev. Immunol.*, 1988, 6:381-405.

Wong et al., "Human GM-CSF: Molecular Cloning of the Complementary DNA and Purification of Natural and Recombinant Proteins," *Science*, 1985, 228:810-815.

Yoshinaga et al., "T-cell co-stimulation through B7RP-1 and ICOS," *Nature*, 1999, 402:827-832.

Experimental data generated by a licensee of the present application.

* cited by examiner

Figure 1

MetArgIlePheAlaValPheIlePheMetThrTyrTrpHisLeuLeuAsnAlaPheThrVal
ThrValProLysAspLeuTyrValValGluTyrGlySerAsnMetThrIleGluCysLysPhe
ProValGluLysGlnLeuAspLeuAlaAlaLeuIleValTyrTrpGluMetGluAspLysAsn
IleIleGlnPheValHisGlyGluGluAspLeuLysValGlnHisSerSerTyrArgGlnArg
AlaArgLeuLeuLysAspGlnLeuSerLeuGlyAsnAlaAlaLeuGlnIleThrAspValLys
LeuGlnAspAlaGlyValTyrArgCysMetIleSerTyrGlyGlyAlaAspTyrLysArgIle
ThrValLysValAsnAlaProTyrAsnLysIleAsnGlnArgIleLeuValValAspProVal
ThrSerGluHisGluLeuThrCysGlnAlaGluGlyTyrProLysAlaGluValIleTrpThr
SerSerAspHisGlnValLeuSerGlyLysThrThrThrThrAsnSerLysArgGluGluLys
LeuPheAsnValThrSerThrLeuArgIleAsnThrThrThrAsnGluIlePheTyrCysThr
PheArgArgLeuAspProGluAsnHisThrAlaGluLeuValIleProGluLeuProLeu
AlaHisProProAsnGluArgThrHisLeuValIleLeuGlyAlaIleLeuLeuCysLeuGly
ValAlaLeuThrPheIlePheArgLeuArgLysGlyArgMetMetAspValLysLysCysGly
IleGlnAspThrAsnSerLysLysGlnSerAspThrHisLeuGluGluThr (SEQ ID NO:3)

Figure 2

MetArgIlePheAlaGlyIleIlePheThrAlaCysCysHisLeuLeuArgAlaPheThrIle
ThrAlaProLysAspLeuTyrValValGluTyrGlySerAsnValThrMetGluCysArgPhe
ProValGluArgGluLeuAspLeuLeuAlaLeuValValTyrTrpGluLysGluAspGluGln
ValIleGlnPheValAlaGlyGluGluAspLeuLysProGlnHisSerAsnPheArgGlyArg
AlaSerLeuProLysAspGlnLeuLeuLysGlyAsnAlaAlaLeuGlnIleThrAspValLys
LeuGlnAspAlaGlyValTyrCysCysIleIleSerTyrGlyGlyAlaAspTyrLysArgIle
ThrLeuLysValAsnAlaProTyrArgLysIleAsnGlnArgIleSerValAspProAlaThr
SerGluHisGluLeuIleCysGlnAlaGluGlyTyrProGluAlaGluValIleTrpThrAsn
SerAspHisGlnProValSerGlyLysArgSerValThrThrSerArgThrGluGlyMetLeu
LeuAsnValThrSerSerLeuArgValAsnAlaThrAlaAsnAspValPheTyrCysThrPhe
TrpArgSerGlnProGlyGlnAsnHisThrAlaGluLeuIleIleProGluLeuProAlaThr
HisProProGlnAsnArgThrHisTrpValLeuLeuGlySerIleLeuLeuPheLeuIleVal
ValSerThrValLeuLeuPheLeuArgLysGlnValArgMetLeuAspValGluLysCysGly
ValGluAspThrSerSerLysAsnArgAsnAspThrGlnPheGluGluThr (SEQ ID NO:4)

Figure 3

MetIlePheLeuLeuLeuMetLeuSerLeuGluLeuGlnLeuHisGlnIleAlaAla
LeuPheThrValThrValProLysGluLeuTyrIleIleGluHisGlySerAsnVal
ThrLeuGluCysAsnPheAspThrGlySerHisValAsnLeuGlyAlaIleThrAla
SerLeuGlnLysValGluAsnAspThrSerProHisArgGluArgAlaThrLeuLeu
GluGluGlnLeuProLeuGlyLysAlaSerPheHisIleProGlnValGlnValArg
AspGluGlyGlnTyrGlnCysIleIleIleTyrGlyValAlaTrpAspTyrLysTyr
LeuThrLeuLysValLysAlaSerTyrArgLysIleAsnThrHisIleLeuLysVal
ProGluThrAspGluValGluLeuThrCysGlnAlaThrGlyTyrProLeuAlaGlu
ValSerTrpProAsnValSerValProAlaAsnThrSerHisSerArgThrProGlu
GlyLeuTyrGlnValThrSerValLeuArgLeuLysProProProGlyArgAsnPhe
SerCysValPheTrpAsnThrHisValArgGluLeuThrLeuAlaSerIleAspLeu
GlnSerGlnMetGluProArgThrHisProThrTrpLeuLeuHisIlePheIlePro
SerCysIleIleAlaPheIlePheIleAlaThrValIleAlaLeuArgLysGlnLeu
CysGlnLysLeuTyrSerSerLysAspThrThrLysArgProValThrThrThrLys
ArgGluValAsnSerAlaIle (SEQ ID NO:5)

Figure 4

MetLeuLeuLeuLeuProIleLeuAsnLeuSerLeuGlnLeuHisProValAlaAla
LeuPheThrValThrAlaProLysGluValTyrThrValAspValGlySerSerVal
SerLeuGluCysAspPheAspArgArgGluCysThrGluLeuGluGlyIleArgAla
SerLeuGlnLysValGluAsnAspThrSerLeuGlnSerGluArgAlaThrLeuLeu
GluGluGlnLeuProLeuGlyLysAlaLeuPheHisIleProSerValGlnValArg
AspSerGlyGlnTyrArgCysLeuValIleCysGlyAlaAlaTrpAspTyrLysTyr
LeuThrValLysValLysAlaSerTyrMetArgIleAspThrArgIleLeuGluVal
ProGlyThrGlyGluValGlnLeuThrCysGlnAlaArgGlyTyrProLeuAlaGlu
ValSerTrpGlnAsnValSerValProAlaAsnThrSerHisIleArgThrProGlu
GlyLeuTyrGlnValThrSerValLeuArgLeuLysProGlnProSerArgAsnPhe
SerCysMetPheTrpAsnAlaHisMetLysGluLeuThrSerAlaIleIleAspPro
LeuSerArgMetGluProLysValProArgThrTrpProLeuHisValPheIlePro
AlaCysThrIleAlaLeuIlePheLeuAlaIleValIleIleGlnArgLysArgIle (SEQ ID NO:6)

Figure 5

```
atgaggatat ttgctgtctt tatattcatg acctactggc atttgctgaa
cgcatttact gtcacggttc ccaaggacct atatgtggta gagtatggta
gcaatatgac aattgaatgc aaattcccag tagaaaaaca attagacctg
gctgcactaa ttgtctattg ggaaatggag gataagaaca ttattcaatt
tgtgcatgga gaggaagacc tgaaggttca gcatagtagc tacagacaga
gggcccggct gttgaaggac cagctctccc tgggaaatgc tgcacttcag
atcacagatg tgaaattgca ggatgcaggg gtgtaccgct gcatgatcag
ctatggtggt gccgactaca agcgaattac tgtgaaagtc aatgccccat
acaacaaaat caaccaaaga attttggttg tggatccagt cacctctgaa
catgaactga catgtcaggc tgagggctac cccaaggccg aagtcatctg
gacaagcagt gaccatcaag tcctgagtgg taagaccacc accaccaatt
ccaagagaga ggagaagctt ttcaatgtga ccagcacact gagaatcaac
acaacaacta atgagatttt ctactgcact tttaggagat tagatcctga
ggaaaaccat acagctgaat tggtcatccc agaactacct ctggcacatc
ctccaaatga aaggactcac ttggtaattc tgggagccat cttattatgc
cttggtgtag cactgacatt catcttccgt ttaagaaaag ggagaatgat
ggatgtgaaa aaatgtggca tccaagatac aaactcaaag aagcaaagtg
atacacattt ggaggagacg taa
```

(SEQ ID NO:7)

Figure 6

```
atgaggatat ttgctggcat tatattcaca gcctgctgtc acttgctacg
ggcgtttact atcacggctc caaaggactt gtacgtggtg gagtatggca
gcaacgtcac gatggagtgc agattccctg tagaacggga gctggacctg
cttgcgttag tggtgtactg ggaaaaggaa gatgagcaag tgattcagtt
tgtggcagga gaggaggacc ttaagcctca gcacagcaac ttcaggggga
gagcctcgct gccaaggac cagcttttga agggaaatgc tgcccttcag
atcacagacg tcaagctgca ggacgcaggc gtttactgct gcataatcag
ctacggtggt gcggactaca agcgaatcac gctgaaagtc aatgccccat
accgcaaaat caaccagaga atttccgtgg atccagccac ttctgagcat
gaactaatat gtcaggccga gggttatcca gaagctgagg taatctggac
aaacagtgac caccaacccg tgagtgggaa gagaagtgtc accacttccc
ggacagaggg gatgcttctc aatgtgacca gcagtctgag ggtcaacgcc
acagcgaatg atgttttcta ctgtacgttt tggagatcac agccagggca
aaaccacaca gcggagctga tcatcccaga actgcctgca acacatcctc
cacagaacag gactcactgg gtgcttctgg gatccatcct gttgttcctc
attgtagtgt ccacggtcct cctcttcttg agaaaacaag tgagaatgct
agatgtggag aaatgtggcg ttgaagatac aagctcaaaa aaccgaaatg
atacacaatt cgaggagacg taa
```

(SEQ ID NO:8)

Figure 7

```
atgatcttcc tcctgctaat gttgagcctg gaattgcagc ttcaccagat
agcagcttta ttcacagtga cagtccctaa ggaactgtac ataatagagc
atggcagcaa tgtgaccctg gaatgcaact ttgacactgg aagtcatgtg
aaccttggag caataacagc cagtttgcaa aaggtggaaa atgatacatc
cccacaccgt gaaagagcca ctttgctgga ggagcagctg cccctaggga
aggcctcgtt ccacatacct caagtccaag tgagggacga aggacagtac
caatgcataa tcatctatgg ggtcgcctgg gactacaagt acctgactct
gaaagtcaaa gcttcctaca ggaaaataaa cactcacatc ctaaaggttc
cagaaacaga tgaggtagag ctcacctgcc aggctacagg ttatcctctg
gcagaagtat cctggccaaa cgtcagcgtt cctgccaaca ccagccactc
caggacccct gaaggcctct accaggtcac cagtgttctg cgcctaaagc
cacccctgg cagaaacttc agctgtgtgt tctggaatac tcacgtgagg
gaacttactt tggccagcat tgaccttcaa agtcagatgg aacccaggac
ccatccaact tggctgcttc acatttcat ccctcctgc atcattgctt
tcattttcat agccacagtg atagccctaa gaaaacaact ctgtcaaaag
ctgtattctt caaagacac aacaaaaga cctgtcacca caacaaagag
ggaagtgaac agtgctatct ga
```

(SEQ ID NO:9)

Figure 8

```
atgctgctcc tgctgccgat actgaacctg agcttacaac ttcatcctgt
agcagcttta ttcaccgtga cagcccctaa agaagtgtac accgtagacg
tcggcagcag tgtgagcctg gagtgcgatt ttgaccgcag agaatgcact
gaactggaag ggataagagc cagtttgcag aaggtagaaa atgatacgtc
tctgcaaagt gaaagagcca ccctgctgga ggagcagctg cccctgggaa
aggctttgtt ccacatccct agtgtccaag tgagagattc cgggcagtac
cgttgcctgg tcatctgcgg ggccgcctgg gactacaagt acctgacggt
gaaagtcaaa gcttcttaca tgaggataga cactaggatc ctggaggttc
caggtacagg ggaggtgcag cttacctgcc aggctagagg ttatcccta
gcagaagtgt cctggcaaaa tgtcagtgtt cctgccaaca ccagccacat
caggaccccc gaaggcctct accaggtcac cagtgttctg cgcctcaagc
ctcagcctag cagaaacttc agctgcatgt tctggaatgc tcacatgaag
gagctgactt cagccatcat tgaccctctg agtcggatgg aacccaaagt
ccccagaacg tggccacttc atgttttcat cccggcctgc accatcgctt
tgatcttcct ggccatagtg ataatccaga gaaagaggat ctag
```

(SEQ ID NO:10)

Figure 9

|        | A' | B | C | C' |
|--------|----|----|----|----|
| hCD86  | LKIQAY....FNETADLPCQFANSQNQSLSELVVFWQDQENLVLNEVY |
| hCD80  | IHVTKE.....VKEVATLSCGH.NVSVEELAQTRIYWQKEK.KMVLTMM |
| hB7-H1 | DLYVVE.....YGSNMTIECKFPVEKQLDLAALIVYWEMEDKNIIQFVH |
| mB7-H1 | DLYVVE.....YGSNVTMECRFPVERELDLLALVVYWEKEDEQVIQFVA |
| hB7-H2 | KEVRAM.....VGSDVELSCACPEGSRFDLNDVVYWQTSESKTVVTYH |
| hB7-H3 | DPVVAL.....VGTDATLCCSPSPEPGFSLAQLNLIWQLTDTQLVHSFA |
| hPD-L2 | ELYIIE.....HGSNVTLECNFDTGSHVNGAITASLQK....VENDTS |
| mPD-L2 | EVYTVD.....VGSSVSLECDFDRRECTELEGIRASLQK....VENDTS |
|        | 26    31           37              50         58        67 69 |
|        | 28                 40              50         56        65 67 |

|        | C" | D | E |
|--------|----|----|----|
| hCD86  | LGKEKF.DSVHSKYMGRTSFDSDS.....WTLRLHNLQIKDKG |
| hCD80  | SGDMNI....WPEYKNRTIFDITN....NLSIVILALRPSDEG |
| hB7-H1 | .GEEDL.KVQHSSYRQRARLLKDQLSLGNAALQITDVKLQDAG |
| mB7-H1 | .GEEDL.KPQHSNFRGRASLPKDQLLKGNAALQITDVKLQDAG |
| hB7-H2 | IPQNSSLENVDSRYRNRALMSPAGLMRGDFSLRLFNVTPQDEQ |
| hB7-H3 | EGQDQG.....SAYANRTALFPDLLAQGNASLRLQRVRVADEG |
| hPD-L2 | PHRERA.....TLLEEQLPLGK.......ASFHIPQVQVRDEG |
| mPD-L2 | LQSERA.....TLLEEQLPLGK.......ALFHIPSVQVRDSG |
|        | 70      80         90        100         110 |
|        | 71      80                   90 |

|        | F | G |  |
|--------|----|----|----|
| hCD86  | LYQCIIHHKKPTGMIRIHQMNSELSVLA | (SEQ ID NO:11) |
| hCD80  | TYECVVLKYEKDAFKREHLAEVTLSVKA | (SEQ ID NO:12) |
| hB7-H1 | VYRCMISYGGADYKRITVKVNAPYNKIN | (SEQ ID NO:13) |
| mB7-H1 | VYCCIISYGGADYKRITLKVNAPYRKIN | (SEQ ID NO:14) |
| hB7-H2 | KFHCLVLSQS.LGFQEVLSVEVTLHVAA | (SEQ ID NO:15) |
| hB7-H3 | SFTCFVSIRDFGSAAVSLQVAAPYSKPS | (SEQ ID NO:16) |
| hPD-L2 | QYQCIIIYGV.AWDYKYLTLKVKASYRK | (SEQ ID NO:17) |
| mPD-L2 | QYRCLVICGA.AWDYKYLTVKVKASYMR | (SEQ ID NO:18) |
|        | 115       124    129       138 |
|        | 101     105    111      120    125 |

SEQUENCE LISTING

```
<160> NUMBER OF SEQ ID NOS: 22

<210> SEQ ID NO 1
<211> LENGTH: 6
<212> TYPE: PRT
<213> ORGANISM: Homo sapiens

<400> SEQUENCE: 1

Met Tyr Pro Pro Pro Tyr
1               5

<210> SEQ ID NO 2
<211> LENGTH: 6
<212> TYPE: PRT
<213> ORGANISM: Homo sapiens

<400> SEQUENCE: 2

Phe Asp Pro Pro Pro Phe
1               5
```

<210> SEQ ID NO 3
<211> LENGTH: 290
<212> TYPE: PRT
<213> ORGANISM: Homo sapiens

<400> SEQUENCE: 3

Met Arg Ile Phe Ala Val Phe Ile Phe Met Thr Tyr Trp His Leu Leu
 1               5                  10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
            275                 280                 285

Glu Thr
    290

<210> SEQ ID NO 4
<211> LENGTH: 290
<212> TYPE: PRT
<213> ORGANISM: Mus musculus

<400> SEQUENCE: 4

Met Arg Ile Phe Ala Gly Ile Ile Phe Thr Ala Cys Cys His Leu Leu
 1               5                  10                  15

Arg Ala Phe Thr Ile Thr Ala Pro Lys Asp Leu Tyr Val Val Glu Tyr
            20                  25                  30

```
Gly Ser Asn Val Thr Met Glu Cys Arg Phe Pro Val Glu Arg Glu Leu
            35                  40                  45

Asp Leu Leu Ala Leu Val Val Tyr Trp Glu Lys Glu Asp Glu Gln Val
 50                  55                  60

Ile Gln Phe Val Ala Gly Glu Glu Asp Leu Lys Pro Gln His Ser Asn
 65                  70                  75                  80

Phe Arg Gly Arg Ala Ser Leu Pro Lys Asp Gln Leu Leu Lys Gly Asn
                 85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
            115                 120                 125

Lys Val Asn Ala Pro Tyr Arg Lys Ile Asn Gln Arg Ile Ser Val Asp
            130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
                180                 185                 190

Thr Ser Ser Leu Arg Val Asn Ala Thr Ala Asn Asp Val Phe Tyr Cys
            195                 200                 205

Thr Phe Trp Arg Ser Gln Pro Gly Gln Asn His Thr Ala Glu Leu Ile
            210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
            275                 280                 285

Glu Thr
  290

<210> SEQ ID NO 5
<211> LENGTH: 273
<212> TYPE: PRT
<213> ORGANISM: Homo sapiens

<400> SEQUENCE: 5

Met Ile Phe Leu Leu Leu Met Leu Ser Leu Glu Leu Gln Leu His Gln
 1               5                  10                  15

Ile Ala Ala Leu Phe Thr Val Thr Val Pro Lys Glu Leu Tyr Ile Ile
             20                  25                  30

Glu His Gly Ser Asn Val Thr Leu Glu Cys Asn Phe Asp Thr Gly Ser
             35                  40                  45

His Val Asn Leu Gly Ala Ile Thr Ala Ser Leu Gln Lys Val Glu Asn
 50                  55                  60

Asp Thr Ser Pro His Arg Glu Arg Ala Thr Leu Leu Glu Glu Gln Leu
 65                  70                  75                  80

Pro Leu Gly Lys Ala Ser Phe His Ile Pro Gln Val Gln Val Arg Asp
                 85                  90                  95

Glu Gly Gln Tyr Gln Cys Ile Ile Ile Tyr Gly Val Ala Trp Asp Tyr
```

-continued

```
                100                 105                 110
Lys Tyr Leu Thr Leu Lys Val Lys Ala Ser Tyr Arg Lys Ile Asn Thr
            115                 120                 125

His Ile Leu Lys Val Pro Glu Thr Asp Glu Val Glu Leu Thr Cys Gln
            130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Gly Arg Asn Phe Ser Cys
            180                 185                 190

Val Phe Trp Asn Thr His Val Arg Glu Leu Thr Leu Ala Ser Ile Asp
            195                 200                 205

Leu Gln Ser Gln Met Glu Pro Arg Thr His Pro Thr Trp Leu Leu His
            210                 215                 220

Ile Phe Ile Pro Ser Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
            245                 250                 255

Thr Thr Lys Arg Pro Val Thr Thr Lys Arg Glu Val Asn Ser Ala
            260                 265                 270

Ile
```

<210> SEQ ID NO 6
<211> LENGTH: 247
<212> TYPE: PRT
<213> ORGANISM: Mus musculus

<400> SEQUENCE: 6

```
Met Leu Leu Leu Leu Pro Ile Leu Asn Leu Ser Leu Gln Leu His Pro
1               5                   10                  15

Val Ala Ala Leu Phe Thr Val Thr Ala Pro Lys Glu Val Tyr Thr Val
            20                  25                  30

Asp Val Gly Ser Ser Val Ser Leu Glu Cys Asp Phe Asp Arg Arg Glu
            35                  40                  45

Cys Thr Glu Leu Glu Gly Ile Arg Ala Ser Leu Gln Lys Val Glu Asn
            50                  55                  60

Asp Thr Ser Leu Gln Ser Glu Arg Ala Thr Leu Leu Glu Glu Gln Leu
65                  70                  75                  80

Pro Leu Gly Lys Ala Leu Phe His Ile Pro Ser Val Gln Val Arg Asp
            85                  90                  95

Ser Gly Gln Tyr Arg Cys Leu Val Ile Cys Gly Ala Ala Trp Asp Tyr
            100                 105                 110

Lys Tyr Leu Thr Val Lys Val Lys Ala Ser Tyr Met Arg Ile Asp Thr
            115                 120                 125

Arg Ile Leu Glu Val Pro Gly Thr Gly Glu Val Gln Leu Thr Cys Gln
            130                 135                 140

Ala Arg Gly Tyr Pro Leu Ala Glu Val Ser Trp Gln Asn Val Ser Val
145                 150                 155                 160

Pro Ala Asn Thr Ser His Ile Arg Thr Pro Glu Gly Leu Tyr Gln Val
                165                 170                 175

Thr Ser Val Leu Arg Leu Lys Pro Gln Pro Ser Arg Asn Phe Ser Cys
            180                 185                 190

Met Phe Trp Asn Ala His Met Lys Glu Leu Thr Ser Ala Ile Ile Asp
```

```
              195                 200                 205
Pro Leu Ser Arg Met Glu Pro Lys Val Pro Arg Thr Trp Pro Leu His
    210                 215                 220

Val Phe Ile Pro Ala Cys Thr Ile Ala Leu Ile Phe Leu Ala Ile Val
225                 230                 235                 240

Ile Ile Gln Arg Lys Arg Ile
            245

<210> SEQ ID NO 7
<211> LENGTH: 873
<212> TYPE: DNA
<213> ORGANISM: Homo sapiens

<400> SEQUENCE: 7
atgaggatat ttgctgtctt tatattcatg acctactggc atttgctgaa cgcatttact      60
gtcacggttc ccaaggacct atatgtggta gagtatggta gcaatatgac aattgaatgc     120
aaattcccag tagaaaaaca attagacctg gctgcactaa ttgtctattg ggaaatggag     180
gataagaaca ttattcaatt tgtgcatgga gaggaagacc tgaaggttca gcatagtagc     240
tacagacaga gggcccggct gttgaaggac cagctctccc tgggaaatgc tgcacttcag     300
atcacagatg tgaaattgca ggatgcaggg gtgtaccgct gcatgatcag ctatggtggt     360
gccgactaca gcgaattac tgtgaaagtc aatgccccat acaacaaaat caaccaaaga     420
attttggttg tggatccagt cacctctgaa catgaactga catgtcaggc tgagggctac     480
cccaaggccg aagtcatctg acaagcagt gaccatcaag tcctgagtgg taagaccacc     540
accaccaatt ccaagagaga ggagaagctt ttcaatgtga ccagcacact gagaatcaac     600
acaacaacta tgagatttt ctactgcact tttaggagat tagatcctga ggaaaaccat     660
acagctgaat tggtcatccc agaactacct ctggcacatc ctccaaatga aggactcac      720 ttggtaattc tgggagccat cttattatgc cttggtgtag cactgacatt catcttccgt     780
ttaagaaaag ggagaatgat ggatgtgaaa aaatgtggca tccaagatac aaactcaaag     840
aagcaaagtg atacacattt ggaggagacg taa                                   873

<210> SEQ ID NO 8
<211> LENGTH: 873
<212> TYPE: DNA
<213> ORGANISM: Mus musculus

<400> SEQUENCE: 8
atgaggatat ttgctggcat tatattcaca gcctgctgtc acttgctacg ggcgtttact      60
atcacggctc caaaggactt gtacgtggtg gagtatggca gcaacgtcac gatggagtgc     120
agattccctg tagaacggga gctggacctg cttgcgttag tggtgtactg ggaaaaggaa     180
gatgagcaag tgattcagtt gtggcagga gaggaggacc ttaagcctca gcacagcaac     240
ttcaggggga gagcctcgct gccaaaggac cagcttttga agggaaatgc tgcccttcag     300
atcacagacg tcaagctgca ggacgcaggc gtttactgct gcataatcag ctacggtggt     360
gcggactaca gcgaatcac gctgaaagtc aatgccccat accgcaaaat caaccagaga     420
atttccgtgg atccagccac ttctgagcat gaactaatat gtcaggccga gggttatcca     480
gaagctgagg taatctggac aaacagtgac caccaacccg tgagtgggaa gagaagtgtc     540
accacttccc ggacagaggg gatgcttctc aatgtgacca gcagtctgag ggtcaacgcc     600
acagcgaatg atgttttcta ctgtacgttt tggagatcac agccagggca aaaccacaca     660
```

-continued

| | |
|---|---|
| gcggagctga tcatcccaga actgcctgca acacatcctc cacagaacag gactcactgg | 720 |
| gtgcttctgg gatccatcct gttgttcctc attgtagtgt ccacggtcct cctcttcttg | 780 |
| agaaaacaag tgagaatgct agatgtggag aaatgtggcg ttgaagatac aagctcaaaa | 840 |
| aaccgaaatg atacacaatt cgaggagacg taa | 873 |

<210> SEQ ID NO 9
<211> LENGTH: 822
<212> TYPE: DNA
<213> ORGANISM: Homo sapiens

<400> SEQUENCE: 9

| | |
|---|---|
| atgatcttcc tcctgctaat gttgagcctg gaattgcagc ttcaccagat agcagcttta | 60 |
| ttcacagtga cagtccctaa ggaactgtac ataatagagc atggcagcaa tgtgaccctg | 120 |
| gaatgcaact ttgacactgg aagtcatgtg aaccttggag caataacagc cagtttgcaa | 180 |
| aaggtggaaa atgatacatc cccacaccgt gaaagagcca ctttgctgga ggagcagctg | 240 |
| cccctaggga aggcctcgtt ccacatacct caagtccaag tgagggacga aggacagtac | 300 |
| caatgcataa tcatctatgg ggtcgcctgg gactacaagt acctgactct gaaagtcaaa | 360 |
| gcttcctaca ggaaaataaa cactcacatc ctaaaggttc agaaacaga tgaggtagag | 420 |
| ctcacctgcc aggctacagg ttatcctctg cagaagtat cctggccaaa cgtcagcgtt | 480 |
| cctgccaaca ccagccactc caggaccccct gaaggcctct accaggtcac cagtgttctg | 540 |
| cgcctaaagc caccccctgg cagaaacttc agctgtgtgt tctggaatac tcacgtgagg | 600 |
| gaacttactt tggccagcat tgaccttcaa agtcagatgg aacccaggac ccatccaact | 660 |
| tggctgcttc acattttcat cccctcctgc atcattgctt tcatttcat agccacagtg | 720 |
| atagccctaa gaaacaact ctgtcaaaag ctgtattctt caaaagacac aacaaaaga | 780 |
| cctgtcacca aacaaagag ggaagtgaac agtgctatct ga | 822 |

<210> SEQ ID NO 10
<211> LENGTH: 744
<212> TYPE: DNA
<213> ORGANISM: Mus musculus

<400> SEQUENCE: 10

| | |
|---|---|
| atgctgctcc tgctgccgat actgaacctg agcttacaac ttcatcctgt agcagcttta | 60 |
| ttcaccgtga cagcccctaa agaagtgtac accgtagacg tcggcagcag tgtgagcctg | 120 |
| gagtgcgatt ttgaccgcag agaatgcact gaactggaag ggataagagc cagtttgcag | 180 |
| aaggtagaaa atgatacgtc tctgcaaagt gaaagagcca ccctgctgga ggagcagctg | 240 |
| cccctgggaa aggctttgtt ccacatccct agtgtccaag tgagagattc cgggcagtac | 300 |
| cgttgcctgg tcatctgcgg ggccgcctgg gactacaagt acctgacggt gaaagtcaaa | 360 |
| gcttcttaca tgaggataga cactaggatc ctggaggttc aggtacaggg gaggtgcag | 420 |
| cttacctgcc aggctagagg ttatccccta gcagaagtgt cctggcaaaa tgtcagtgtt | 480 |
| cctgccaaca ccagccacat caggaccccc gaaggcctct accaggtcac cagtgttctg | 540 |
| cgcctcaagc ctcagcctag cagaaacttc agctgcatgt tctggaatgc tcacatgaag | 600 |
| gagctgactt cagccatcat tgaccctctg agtcggatgg aacccaaagt ccccagaacg | 660 |
| tggccacttc atgtttttcat cccggcctgc accatcgctt tgatcttcct ggccatagtg | 720 |
| ataatccaga gaaagaggat ctag | 744 |

```
<210> SEQ ID NO 11
<211> LENGTH: 109
<212> TYPE: PRT
<213> ORGANISM: Homo sapiens

<400> SEQUENCE: 11

Leu Lys Ile Gln Ala Tyr Phe Asn Glu Thr Ala Asp Leu Pro Cys Gln
 1               5                  10                  15

Phe Ala Asn Ser Gln Asn Gln Ser Leu Ser Glu Leu Val Val Phe Trp
                20                  25                  30

Gln Asp Gln Glu Asn Leu Val Leu Asn Glu Val Tyr Leu Gly Lys Glu
            35                  40                  45

Lys Phe Asp Ser Val His Ser Lys Tyr Met Gly Arg Thr Ser Phe Asp
    50                  55                  60

Ser Asp Ser Trp Thr Leu Arg Leu His Asn Leu Gln Ile Lys Asp Lys
65                  70                  75                  80

Gly Leu Tyr Gln Cys Ile Ile His His Lys Lys Pro Thr Gly Met Ile
                85                  90                  95

Arg Ile His Gln Met Asn Ser Glu Leu Ser Val Leu Ala
            100                 105

<210> SEQ ID NO 12
<211> LENGTH: 105
<212> TYPE: PRT
<213> ORGANISM: Homo sapiens

<400> SEQUENCE: 12

Ile His Val Thr Lys Glu Val Lys Glu Val Ala Thr Leu Ser Cys Gly
 1               5                  10                  15

His Asn Val Ser Val Glu Glu Leu Ala Gln Thr Arg Ile Tyr Trp Gln
                20                  25                  30

Lys Glu Lys Lys Met Val Leu Thr Met Met Ser Gly Asp Met Asn Ile
            35                  40                  45

Trp Pro Glu Tyr Lys Asn Arg Thr Ile Phe Asp Ile Thr Asn Asn Leu
    50                  55                  60

Ser Ile Val Ile Leu Ala Leu Arg Pro Ser Asp Glu Gly Thr Tyr Glu
65                  70                  75                  80

Cys Val Val Leu Lys Tyr Glu Lys Asp Ala Phe Lys Arg Glu His Leu
                85                  90                  95

Ala Glu Val Thr Leu Ser Val Lys Ala
            100                 105

<210> SEQ ID NO 13
<211> LENGTH: 113
<212> TYPE: PRT
<213> ORGANISM: Homo sapiens

<400> SEQUENCE: 13

Asp Leu Tyr Val Val Glu Tyr Gly Ser Asn Met Thr Ile Glu Cys Lys
 1               5                  10                  15

Phe Pro Val Glu Lys Gln Leu Asp Leu Ala Ala Leu Ile Val Tyr Trp
                20                  25                  30

Glu Met Glu Asp Lys Asn Ile Ile Gln Phe Val His Gly Glu Glu Asp
            35                  40                  45

Leu Lys Val Gln His Ser Ser Tyr Arg Gln Arg Ala Arg Leu Leu Lys
    50                  55                  60

Asp Gln Leu Ser Leu Gly Asn Ala Ala Leu Gln Ile Thr Asp Val Lys
65                  70                  75                  80
```

```
Leu Gln Asp Ala Gly Val Tyr Arg Cys Met Ile Ser Tyr Gly Gly Ala
                85                  90                  95

Asp Tyr Lys Arg Ile Thr Val Lys Val Asn Ala Pro Tyr Asn Lys Ile
            100                 105                 110

Asn
```

<210> SEQ ID NO 14
<211> LENGTH: 113
<212> TYPE: PRT
<213> ORGANISM: Mus musculus

<400> SEQUENCE: 14

```
Asp Leu Tyr Val Val Glu Tyr Gly Ser Asn Val Thr Met Glu Cys Arg
 1               5                  10                  15

Phe Pro Val Glu Arg Glu Leu Asp Leu Leu Ala Leu Val Val Tyr Trp
                20                  25                  30

Glu Lys Glu Asp Glu Gln Val Ile Gln Phe Val Ala Gly Glu Glu Asp
            35                  40                  45

Leu Lys Pro Gln His Ser Asn Phe Arg Gly Arg Ala Ser Leu Pro Lys
        50                  55                  60

Asp Gln Leu Leu Lys Gly Asn Ala Ala Leu Gln Ile Thr Asp Val Lys
65                  70                  75                  80

Leu Gln Asp Ala Gly Val Tyr Cys Cys Ile Ile Ser Tyr Gly Gly Ala
                85                  90                  95

Asp Tyr Lys Arg Ile Thr Leu Lys Val Asn Ala Pro Tyr Arg Lys Ile
            100                 105                 110

Asn
```

<210> SEQ ID NO 15
<211> LENGTH: 114
<212> TYPE: PRT
<213> ORGANISM: Homo sapiens

<400> SEQUENCE: 15

```
Lys Glu Val Arg Ala Met Val Gly Ser Asp Val Glu Leu Ser Cys Ala
 1               5                  10                  15

Cys Pro Glu Gly Ser Arg Phe Asp Leu Asn Asp Val Tyr Val Tyr Trp
                20                  25                  30

Gln Thr Ser Glu Ser Lys Thr Val Val Thr Tyr His Ile Pro Gln Asn
            35                  40                  45

Ser Ser Leu Glu Asn Val Asp Ser Arg Tyr Arg Asn Arg Ala Leu Met
        50                  55                  60

Ser Pro Ala Gly Leu Met Arg Gly Asp Phe Ser Leu Arg Leu Phe Asn
65                  70                  75                  80

Val Thr Pro Gln Asp Glu Gln Lys Phe His Cys Leu Val Leu Ser Gln
                85                  90                  95

Ser Leu Gly Phe Gln Glu Val Leu Ser Val Glu Val Thr Leu His Val
            100                 105                 110

Ala Ala
```

<210> SEQ ID NO 16
<211> LENGTH: 110
<212> TYPE: PRT
<213> ORGANISM: Homo sapiens

<400> SEQUENCE: 16

Asp Pro Val Val Ala Leu Val Gly Thr Asp Ala Thr Leu Cys Cys Ser
1               5                   10                  15

Pro Ser Pro Glu Pro Gly Phe Ser Leu Ala Gln Leu Asn Leu Ile Trp
                20                  25                  30

Gln Leu Thr Asp Thr Gln Leu Val His Ser Phe Ala Glu Gly Gln Asp
            35                  40                  45

Gln Gly Ser Ala Tyr Ala Asn Arg Thr Ala Leu Phe Pro Asp Leu Leu
        50                  55                  60

Ala Gln Gly Asn Ala Ser Leu Arg Leu Gln Arg Val Arg Val Ala Asp
65                  70                  75                  80

Glu Gly Ser Phe Thr Cys Phe Val Ser Ile Arg Asp Phe Gly Ser Ala
                85                  90                  95

Ala Val Ser Leu Gln Val Ala Ala Pro Tyr Ser Lys Pro Ser
            100                 105                 110

<210> SEQ ID NO 17
<211> LENGTH: 98
<212> TYPE: PRT
<213> ORGANISM: Homo sapiens

<400> SEQUENCE: 17

Glu Leu Tyr Ile Ile Glu His Gly Ser Asn Val Thr Leu Glu Cys Asn
1               5                   10                  15

Phe Asp Thr Gly Ser His Val Asn Leu Gly Ala Ile Thr Ala Ser Leu
                20                  25                  30

Gln Lys Val Glu Asn Asp Thr Ser Pro His Arg Glu Arg Ala Thr Leu
            35                  40                  45

Leu Glu Glu Gln Leu Pro Leu Gly Lys Ala Ser Phe His Ile Pro Gln
        50                  55                  60

Val Gln Val Arg Asp Glu Gly Gln Tyr Gln Cys Ile Ile Ile Tyr Gly
65                  70                  75                  80

Val Ala Trp Asp Tyr Lys Tyr Leu Thr Leu Lys Val Lys Ala Ser Tyr
                85                  90                  95

Arg Lys

<210> SEQ ID NO 18
<211> LENGTH: 98
<212> TYPE: PRT
<213> ORGANISM: Mus musculus

<400> SEQUENCE: 18

Glu Val Tyr Thr Val Asp Val Gly Ser Ser Val Ser Leu Glu Cys Asp
1               5                   10                  15

Phe Asp Arg Arg Glu Cys Thr Glu Leu Glu Gly Ile Arg Ala Ser Leu
                20                  25                  30

Gln Lys Val Glu Asn Asp Thr Ser Leu Gln Ser Glu Arg Ala Thr Leu
            35                  40                  45

Leu Glu Glu Gln Leu Pro Leu Gly Lys Ala Leu Phe Asp Ile Pro Ser
        50                  55                  60

Val Gln Val Arg Asp Ser Gly Gln Tyr Arg Cys Leu Val Ile Cys Gly
65                  70                  75                  80

Ala Ala Trp Asp Tyr Lys Tyr Leu Thr Val Lys Val Lys Ala Ser Tyr
                85                  90                  95

Met Arg

<210> SEQ ID NO 19

```
<211> LENGTH: 25
<212> TYPE: PRT
<213> ORGANISM: Artificial Sequence
<220> FEATURE:
<223> OTHER INFORMATION: Consensus

<400> SEQUENCE: 19

Met Ala Ile Ser Gly Val Pro Val Leu Gly Phe Phe Ile Ile Ala Val
1               5                   10                  15

Leu Met Ser Ala Gln Glu Ser Trp Ala
            20                  25

<210> SEQ ID NO 20
<211> LENGTH: 5
<212> TYPE: PRT
<213> ORGANISM: Artificial Sequence
<220> FEATURE:
<223> OTHER INFORMATION: Consensus

<400> SEQUENCE: 20

Lys Phe Glu Arg Gln
1               5

<210> SEQ ID NO 21
<211> LENGTH: 15
<212> TYPE: PRT
<213> ORGANISM: Artificial Sequence
<220> FEATURE:
<223> OTHER INFORMATION: Consensus

<400> SEQUENCE: 21

Met Asp Asp Gln Arg Asp Leu Ile Ser Asn Asn Glu Gln Leu Pro
1               5                   10                  15

<210> SEQ ID NO 22
<211> LENGTH: 4
<212> TYPE: PRT
<213> ORGANISM: Artificial Sequence
<220> FEATURE:
<223> OTHER INFORMATION: Consensus

<400> SEQUENCE: 22

Lys Asp Glu Leu
1
```

B7-H1 VARIANTS

CROSS-REFERENCE TO RELATED APPLICATIONS

This application claims priority from U.S. Provisional Application Ser. No. 60/416,203, filed Oct. 4, 2002.

STATEMENT AS TO FEDERALLY SPONSORED RESEARCH

Funding for the work described herein was provided in part by the National Institutes of Health, grant numbers CA97085, CA85721, and CA79915. The federal government may have certain rights in the invention.

TECHNICAL FIELD

This invention relates to materials and methods for enhancing T cell activation.

BACKGROUND

Antigen-specific activation and proliferation of lymphocytes are regulated by both positive and negative signals from costimulatory molecules. The most extensively characterized T cell costimulatory pathway is B7-CD28, in which B7-1 (CD80) and B7-2 (CD86) each can engage the stimulatory CD28 receptor and the inhibitory CTLA-4 (CD152) receptor. In conjunction with signaling through the T cell receptor, CD28 ligation increases antigen-specific proliferation of T cells, enhances production of cytokines, stimulates differentiation and effector function, and promotes survival of T cells (Lenshow et al. (1996) *Annu. Rev. Immunol.* 14:233-258; Chambers and Allison (1997) *Curr. Opin. Immunol.* 9:396-404; and Rathmell and Thompson (1999) *Annu. Rev. Immunol.* 17:781-828). In contrast, signaling through CTLA-4 is thought to deliver a negative signal that inhibits T cell proliferation, IL-2 production, and cell cycle progression (Krummel and Allison (1996) *J. Exp. Med.* 183:2533-2540; and Walunas et al. (1996) *J. Exp. Med.* 183:2541-2550). Other members of the B7 family include B7-H1 (Dong et al. (1999) *Nature Med.* 5:1365-1369; and Freeman et al. (2000) *J. Exp. Med.* 192:1-9), B7-DC (Tseng et al. (2001) *J. Exp. Med.* 193:839-846; and Latchman et al. (2001) *Nature Immunol.* 2:261-268), B7-H2 (Wang et al. (2000) *Blood* 96:2808-2813; Swallow et al. (1999) *Immunity* 11:423-432; and Yoshinaga et al. (1999) *Nature* 402:827-832), and B7-H3 (Chapoval et al. (2001) *Nature Immunol.* 2:269-274). B7-H1 and B7-DC are ligands for PD-1, B7-H2 is a ligand for ICOS, and B7-H3 remains at this time an orphan ligand (Dong et al. (2003) *Immunol. Res.* 28:39-48).

B7 family molecules are expressed on the cell surface as homodimers with a membrane proximal constant IgC domain and a membrane distal IgV domain. Receptors for these ligands share a common extracellular IgV-like domain. Interactions of receptor-ligand pairs are mediated predominantly through residues in the IgV domains of the ligands and receptors (Schwartz et al. (2002) *Nature Immunol.* 3:427-434). In general, IgV domains are described as having two sheets that each contain a layer of β-strands (Williams and Barclay (1988) *Annu. Rev. Immunol.* 6:381-405). The front and back sheets of CTLA-4 contain strands A'GFCC' and ABEDC," respectively (Ostrov et al. (2000) *Science* 290:816-819), whereas the front and back sheets of the B7 IgV domains are composed of strands AGFCC'C" and BED, respectively (Schwartz et al. (2001) *Nature* 410:604-608; Stamper et al. (2001) *Nature* 410:608-611; and Ikemizu et al. (2000) *Immunity* 12:51-60). Crystallographic analysis revealed that the CTLA-4/B7 binding interface is dominated by the interaction of the CDR3-analogous loop from CTLA-4, composed of a MYPPPY (SEQ ID NO:1) motif, with a surface on B7 formed predominately by the G, F, C, C' and C" strands (Schwartz et al. (2001) supra; and Stamper et al. supra). Data from amino acid homologies, mutation, and computer modeling provide support for the concept that this motif also is a major B7-binding site for CD28 (Bajorath et al. (1997) *J. Mol. Graph. Model.* 15:135-139). Although the MYPPPY motif is not conserved in ICOS, studies have indicated that a related motif having the sequence FDPPPF (SEQ ID NO:2) and located at the analogous position is a major determinant for binding of ICOS to B7-H2 (Wand et al. (2002) *J. Exp. Med.* 195:1033-1041).

B7-H1 (also called PD-L1) and B7-DC (also called PD-L2) are relatively new members of the B7 family, and have amino acid sequences that are about 34% identical to each other. Human and mouse orthologues of these molecules share about 70% amino acid identity (i.e., the human and mouse B7-H1 amino acid sequences are about 70% identical, and the human and mouse B7-DC amino acid sequences are about 70% identical). While B7-H1 and B7-DC transcripts are found in various tissues (Dong et al. (1999) supra; Latchman et al. supra; and Tamura (2001) *Blood* 97:1809-1816), the expression profiles of the proteins are quite distinct. Expression of B7-H1 protein, although essentially not found in normal tissues other than macrophage-like cells, can be induced in a variety of tissues and cell types (Dong et al. (1999) supra; Tamura et al. supra; and Ishida et al. (2000) *Immunol. Lett.* 84:57-62). In contrast, B7-DC is expressed only in dendritic cells and monocytes (Tseng et al. supra; and Ishida et al. supra).

SUMMARY

The invention provides materials and methods for enhancing a costimulatory response, enhancing T cell activation, and inhibiting interaction between a costimulatory molecule and PD-1. For example, the invention provides purified variant costimulatory polypeptides that have altered binding affinity for PD-1, but that retain substantial costimulatory activity. Since it is likely that the interaction of costimulatory molecules such as B7-H1 and B7-DC with PD-1 suppresses an immune response, variant B7-H1 and variant B7-DC polypeptides with decreased binding affinity for PD-1 can be useful to enhance an immune response.

Methods of the invention can be used to enhance an immune response, enhance T cell activation, or inhibit binding of costimulatory polypeptides to PD-1, for example. Such methods can involve contacting a T cell with any of the purified variant costimulatory polypeptides or fragments provided herein. The T cell can be contacted in vitro or in vivo (e.g., in a mammal such as a mouse or a human). In some embodiments, the T cell can be contacted with a host cell [e.g., an antigen presenting cell (APC)] transfected or transduced with a nucleic acid encoding a polypeptide of the invention. If the T cell is contacted in a mammal, the host cell can be from that mammal or from another mammal. For example, the host cell can be from another mammal of the same species (e.g., another mammal that is histocompatible with the mammal to which the cells are being administered).

In one aspect, the invention provides a purified variant costimulatory polypeptide, wherein the variant polypeptide is a variant of a wild-type costimulatory polypeptide that binds to PD-1 and has reduced binding affinity for PD-1 compared to the wild-type costimulatory polypeptide, wherein the binding affinity is reduced by at least 50 percent as compared to the binding affinity of the wild-type costimulatory polypeptide, and wherein the costimulatory polypeptide retains substantial costimulatory activity. The variant costimulatory polypeptide can contain a substitution of one or more (e.g., two, three, four, five, six, seven, eight, nine, ten, or more than ten) amino acids of the wild-type polypeptide.

The wild-type polypeptide can be a B7-H1 polypeptide [e.g., murine B7-H1 (SEQ ID NO:4)]. The purified variant costimulatory polypeptide can contain a substitution of the amino acid at position 67 of SEQ ID NO:4. The substitution can involve replacing the amino acid at position 67 of SEQ ID NO:4 with an alanine residue. The purified variant costimulatory polypeptide can contain a substitution of the amino acid at position 126 of SEQ ID NO:4. The substitution can involve replacing the amino acid at position 126 of SEQ ID NO:4 with an alanine residue. The purified variant costimulatory polypeptide can contain a substitution of the amino acid at position 37 of SEQ ID NO:4. The substitution can involve replacing the amino acid at position 37 of SEQ ID NO:4 with a tyrosine residue. The purified variant costimulatory polypeptide can contain a substitution of the amino acid at position 115 of SEQ ID NO:4. The substitution can involve replacing the amino acid at position 115 of SEQ ID NO:4 with an alanine residue. The purified variant costimulatory polypeptide can contain a substitution of the amino acid at position 124 of SEQ ID NO:4. The substitution can involve replacing the amino acid at position 124 of SEQ ID NO:4 with a serine residue.

The wild-type polypeptide can be a B7-DC polypeptide [e.g., murine B7-DC (SEQ ID NO:6)]. The purified variant costimulatory polypeptide can contain a substitution of the amino acid at position 111 of SEQ ID NO:6. The substitution can involve replacing the amino acid at position 111 of SEQ ID NO:6 with a serine residue. The purified variant costimulatory polypeptide can contain a substitution of the amino acid at position 113 of SEQ ID NO:6. The substitution can involve replacing the amino acid at position 113 of SEQ ID NO:6 with a serine residue. The purified variant costimulatory polypeptide can contain a substitution of the amino acid at position 56 of SEQ ID NO:6. The substitution can involve replacing the amino acid at position 56 of SEQ ID NO:6 with a serine residue. The purified variant costimulatory polypeptide can contain a substitution of the amino acid at position 67 of SEQ ID NO:6. The substitution can involve replacing the amino acid at position 67 of SEQ ID NO:6 with a tyrosine residue. The purified variant costimulatory polypeptide can contain a substitution of the amino acid at position 71 of SEQ ID NO:6. The substitution can involve replacing the amino acid at position 71 of SEQ ID NO:6 with a serine residue. The purified variant costimulatory polypeptide can contain a substitution of the amino acid at position 101 of SEQ ID NO:6. The substitution can involve replacing the amino acid at position 101 of SEQ ID NO:6 with a serine residue. The purified variant costimulatory polypeptide can contain a substitution of the amino acid at position 105 of SEQ ID NO:6. The substitution can involve replacing the amino acid at position 105 of SEQ ID NO:6 with an alanine residue.

The invention also provides a purified variant costimulatory polypeptide, wherein the variant polypeptide is a variant of a wild-type costimulatory polypeptide that binds to PD-1 and has increased binding affinity for PD-1 compared to the wild-type costimulatory polypeptide, wherein the affinity is increased by at least 50 percent as compared to the affinity of the wild-type costimulatory polypeptide, and wherein the costimulatory polypeptide retains substantial costimulatory activity. The variant costimulatory polypeptide can contain a substitution of one or more amino acids of the wild-type polypeptide. The wild-type polypeptide can be a B7-H1 polypeptide [e.g., murine B7-H1 (SEQ ID NO:4)]. The purified variant costimulatory polypeptide can contain a substitution of the amino acid at position 58 of SEQ ID NO:4. The purified variant costimulatory polypeptide can contain a substitution of the amino acid at position 69 of SEQ ID NO:4. The purified variant costimulatory polypeptide can contain a substitution of the amino acid at position 113 of SEQ ID NO:4. The wild-type polypeptide can be a B7-DC polypeptide [e.g., murine B7-DC (SEQ ID NO:6)]. The purified variant costimulatory polypeptide can contain a substitution of the amino acid at position 58 of SEQ ID NO:6.

In another aspect, the invention features an isolated nucleic acid molecule containing a nucleic acid sequence that encodes any of the variant costimulatory polypeptides provided herein. The invention also features a vector containing the nucleic acid. The nucleic acid sequence can be operably linked to an expression control sequence in the vector. In addition, the invention features a host cell containing the vector of the invention.

In another aspect, the invention features a method for enhancing T cell activation. The method can include contacting a T cell with any of the purified variant costimulatory polypeptides provided by the invention. The contacting can be in vitro. The T cell can be in a mammal. The method can include administering the variant polypeptide to the mammal. Alternatively, the method can involve administering a nucleic acid encoding the variant polypeptide to the mammal. The method can include administering a cell transfected or transduced with the nucleic acid to the mammal, wherein the cell is a cell, or a progeny of a cell, that prior to the transfection or the transduction, was obtained from the mammal. The mammal can be a human.

In yet another aspect, the invention features a polypeptide fragment of murine B7-H1 (SEQ ID NO:4), wherein the polypeptide fragment inhibits binding of murine B7-H1 to murine PD-1. The polypeptide fragment can contain, for example, amino acids 67-69, amino acids 113-115, or amino acids 124-126 of SEQ ID NO:4. The polypeptide fragment can also contain amino acids 62-69 of SEQ ID NO:4.

The invention also features a method of inhibiting the interaction between PD-1 and B7-H1. The method can include contacting a PD-1 polypeptide with a B7-H1 polypeptide fragment provided herein. The PD-1 can be in vitro or in a mammal. The method can involve administering the polypeptide fragment to the mammal, or the method can involve administering a nucleic acid encoding the polypeptide fragment to the mammal. The method can involve administering a cell transfected or transduced with the nucleic acid to the mammal, wherein the cell is a cell, or a progeny of a cell, that prior to the transfection or the transduction, was obtained from the mammal. The mammal can be a human.

In another aspect, the invention features a polypeptide fragment of murine B7-DC (SEQ ID NO:6), wherein the polypeptide inhibits binding of murine B7-DC to murine PD-1. The polypeptide fragment can contain, for example, amino acids 67-71, amino acids 101-105, or amino acids 111-113 of SEQ ID NO:6. The polypeptide fragment can also contain amino acids 101-113 of SEQ ID NO:6.

In another aspect, the invention features a method of inhibiting the interaction between PD-1 and B7-DC. The method can include contacting a PD-1 polypeptide with a B7-DC polypeptide fragment provided herein. The PD-1 can be in vitro or in a mammal. The method can involve administering the polypeptide fragment to the mammal. The method can involve administering a nucleic acid encoding the polypeptide fragment to the mammal. The method can involve administering a cell transfected or transduced with the nucleic acid to the mammal, wherein the cell is a cell, or a progeny of a cell, that prior to the transfection or the transduction, was obtained from the mammal. The mammal can be a human.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a depiction of the full-length, immature amino acid sequence of human B7-H1 (hB7-H1; SEQ ID NO:3).

FIG. 2 is a depiction of the full-length, immature amino acid sequence of mouse B7-H1 (mB7-H1; SEQ ID NO:4).

FIG. 3 is a depiction of the full-length, immature amino acid sequence of human B7-DC (hB7-DC; SEQ ID NO:5).

FIG. 4 is a depiction of the full-length, immature amino acid sequence of mouse B7-DC (mB7-DC; SEQ ID NO:6).

FIG. 5 is a depiction of a nucleotide sequence (SEQ ID NO:7) encoding a full-length, immature human B7-H1 polypeptide having the amino acid sequence shown in FIG. 1.

FIG. 6 is a depiction of a nucleotide sequence (SEQ ID NO:8) encoding a full-length, immature mouse B7-H1 polypeptide having the amino acid sequence shown in FIG. 2.

FIG. 7 is a depiction of a nucleotide sequence (SEQ ID NO:9) encoding a full-length, immature human B7-DC polypeptide having the amino acid sequence shown in FIG. 3.

FIG. 8 is a depiction of a nucleotide sequence (SEQ ID NO:10) encoding a full-length, immature mouse B7-DC polypeptide having the amino acid sequence shown in FIG. 4.

FIG. 9 is a structure-oriented sequence alignment of B7 molecules. The alignment includes sequences from the N-terminal IgV domains of human CD86 (hCD86), human CD80 (hCD80), human B7-H1 (hB7-H1), mouse B7-H1 (mB7-H1), human B7-H2 (hB7-H2), human B7-H3 (hB7-H3), human B7-DC (hPD-L2), and mouse B7-DC (mPD-L2) (SEQ ID NOs:11-18, respectively). β-strands observed in the x-ray structures of CD80 and CD86 are labeled (A'-G), and residue positions most conserved across the B7 family (e.g., large hydrophobic, charged/polar, or cysteine residues) are shaded. Potential N-linked glycosylation sites are boxed. CD86 residues shown in italics are involved in formation of the crystallographic homodimer interface, which is conserved in CD80, and residues shown in bold italics participate in CTLA-4 binding in the structure of the complex. Residue positions in mB7-H1 and mB7-DC that are most important for PD-1 binding, based on mutagenesis studies, are underlined and shown in bold type. Residues in mB7-H1 that, when mutagenized, demonstrated increased avidity for PD-1 are circled. Residue numbers indicate positions within mB7-H1 (upper numbers) and mB7-DC (lower numbers).

FIG. 10A shows results for binding of B7-H1Ig and B7-H1Ig mutants to immobilized PD-11 g, while FIG. 10B shows results for binding of B7-DCIg and B7-DCIg mutants to immobilized PD-1Ig.

DETAILED DESCRIPTION

Figure 10A:
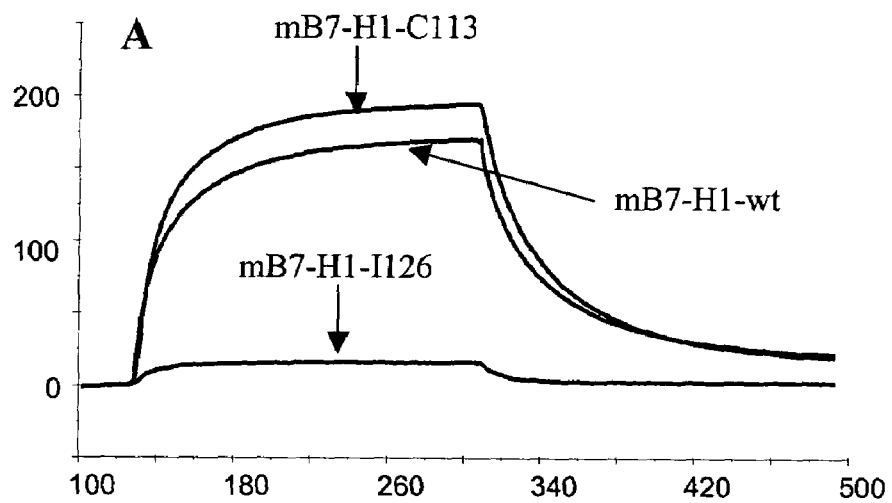
FIGS. 10A and 10B are line graphs showing results from surface plasmon resonance analysis of B7-H1 and B7-DC binding to PD-1.

The invention provides materials and methods for enhancing a costimulatory response, enhancing T cell activation, and inhibiting interaction between a costimulatory molecule and PD-1. For example, the invention provides purified variant costimulatory polypeptides that have altered binding affinity for PD-1, but that retain substantial costimulatory activity. Since it is likely that the interaction of costimulatory molecules such as B7-H1 and B7-DC with PD-1 suppresses an immune response, variant B7-H1 and variant B7-DC polypeptides with decreased binding affinity for PD-1 can be useful to enhance an immune response.

1. Purified Polypeptides

Purified costimulatory polypeptides (e.g., purified B7-H1 and B7-DC polypeptides) are provided herein. As used herein, the term "polypeptide" refers to a chain of amino acids of any length, regardless of modification (e.g., phosphorylation or glycosylation). A "costimulatory polypeptide" is a polypeptide that, upon interaction with a cell-surface molecule on a T cell, enhances a T cell response (e.g., stimulates T cell proliferation and/or cytokine release). The T cell response that results from the interaction typically is greater than the response in the absence of the costimulatory polypeptide. The response of the T cell in the absence of the costimulatory polypeptide can be no response or can be a response significantly lower than in the presence of the costimulatory polypeptide. It is understood that the response of the T cell can be an effector (e.g., CTL or antibody-producing B cell) response, a helper response providing help for one or more effector (e.g., CTL or antibody-producing B cell) responses, or a suppressive response.

A costimulatory polypeptide can be a full-length costimulatory molecule, or can it be a portion (i.e., a functional fragment) of a costimulatory molecule. In some embodiments, a costimulatory polypeptide can be a variant of a full-length, immature B7-H1 polypeptide having the amino acid sequence shown in FIG. 1 or FIG. 2 (SEQ ID NO:3 and SEQ ID NO:4, respectively), or a variant of a full-length, immature B7-DC polypeptide having the amino acid sequence shown in FIG. 3 or FIG. 4 (SEQ ID NO:5 and SEQ ID NO:6, respectively). Alternatively, a costimulatory molecule of the invention can have, for example, a variant amino acid sequence from amino acid residue 20, 21, 22, 23, 24, 25, 26, 27, 28, 29, 30, 31, or 32 to (a) amino acid residue 290 of SEQ ID NO:3 or SEQ ID NO:4, (b) amino acid residue 273 of SEQ ID NO:5, or (c) amino acid residue 247 of SEQ ID NO:6. A costimulatory polypeptide that is a portion of a full-length costimulatory molecule typically has at least 20 percent (e.g., at least 20 percent, 30 percent, 40 percent, 50 percent, 60 percent, 70 percent, 80 percent, 90 percent, 95 percent, 98 percent, 99 percent, 100 percent, or even more than 100 percent) of the costimulatory activity of the full-length costimulatory molecule.

The costimulatory polypeptides provided herein can be variant polypeptides (e.g., variant B7-H1 or B7-DC polypeptides). As used herein, a "variant" costimulatory polypeptide contains at least one amino acid sequence alteration as compared to the amino acid sequence of the corresponding wild-type costimulatory polypeptide (e.g., a polypeptide having the amino acid sequence set forth in any of SEQ ID NOs:3-6). An amino acid sequence alteration can be, for example, a substitution, a deletion, or an insertion of one or more amino acids. With respect to SEQ ID NO:4, for example, a variant B7-H1 polypeptide can contain, without limitation, a substitution at position 67 (e.g., an alanine substitution for phenylalanine at position 67), a substitution at position 126 (e.g., an alanine substitution for isoleucine as position 126), a substitution at position 37 (e.g., a tyrosine substitution for threonine at position 37), a substitution at position 115 (e.g., an alanine substitution for isoleucine at position 115), or a substitution at position 124 (e.g., a serine substitution for lysine at position 124). With respect to SEQ ID NO:6, a variant B7-DC polypeptide can contain, without limitation, a substitution at position 111 (e.g., a serine substitution for aspartic acid at position 111), a substitution at position 113 (e.g., a serine substitution for lysine at position 113), a substitution at position 56 (e.g., a serine substitution for arginine at position 56), a substitution at position 67 (e.g., a tyrosine substitution for serine at position 67), a substitution at position 71 (e.g., a serine substitution for glutamic acid at position 71), a substitution at position 101 (e.g., a serine substitution for arginine at position 101), or a substitution at position 105 (e.g., an alanine substitution for isoleucine at position 105). It is understood, however, that the recited substitutions can be made using any amino acid or amino acid analog. For example, the substitutions at the recited positions can be made with any of the naturally-occurring amino acids (e.g., alanine, aspartic acid, asparagine, arginine, cysteine, glycine, glutamic acid, glutamine, histidine, leucine, valine, isoleucine, lysine, methionine, proline, threonine, serine, phenylalanine, tryptophan, or tyrosine).

While the substitutions described herein are with respect to mouse B7-H1 and mouse B7-DC, it is noted that one of ordinary skill in the art could readily make equivalent alterations in the corresponding polypeptides from other species (e.g., rat, hamster, guinea pig, gerbil, rabbit, dog, cat, horse, pig, sheep, cow, non-human primate, or human). For example, a variant human B7-H1 polypeptide can contain a substitution at position 67, 126, 37, or 124 with respect to the amino acid sequence set forth in SEQ ID NO:3, and a variant human B7-DC polypeptide can contain a substitution at position 111, 113, 67, 71, or 105 with respect to the amino acid sequence set forth in SEQ ID NO:5. Thus, the invention features variants of B7-H1 and B7-DC from all the above mammals, nucleic acids (e.g., DNA or RNA) encoding the variant B7-H1 and variant B7-DC polypeptides, vectors containing the nucleic acids, host cells containing the vectors, and methods of using the variants, the nucleic acids, and the host cells.

A variant costimulatory polypeptide of the invention can have reduced binding affinity for PD-1 as compared to the binding affinity of the corresponding wild-type costimulatory polypeptide. The binding affinity of a variant typically is reduced by at least 50 percent (e.g., at least 50 percent, 55 percent, 60 percent, 70 percent, 75 percent, 80 percent, 90 percent, 95 percent, 99 percent, or more than 99 percent) as compared to the binding affinity of the corresponding wild-type polypeptide. In addition, a variant costimulatory polypeptide with reduced binding affinity for PD-1 can retain substantial costimulatory activity. For example, a variant costimulatory polypeptide can have at least 20 percent (e.g., at least 20 percent, 25 percent, 30 percent, 40 percent, 50 percent, 60 percent, 75 percent, 90 percent, 100 percent, or more than 100 percent) of the level of costimulatory activity exhibited by the corresponding wild-type costimulatory polypeptide. Costimulatory activity can be measured by any of a number of methods, including those disclosed herein (e.g., T cell proliferation and cytokine assays).

The invention also provides polypeptides that are fragments of full-length costimulatory molecules (e.g., costimulatory molecules having the amino acid sequences set forth in SEQ ID NOs:3-6). Such polypeptide fragments typically contain a region of a costimulatory polypeptide that is important for binding affinity for PD-1. For example, a polypeptide fragment of mouse B7-H1 (SEQ ID NO:4) can contain amino acids 67-69, 113-115, or 124-126. A polypeptide fragment of mouse B7-DC can contain, for example, amino acids 67-71, 101-105, or 111-113. Without being bound by a particular mechanism, these fragments can be useful to inhibit the binding of a costimulatory polypeptide (e.g., a full-length, native costimulatory polypeptide) to PD-1 and consequent activation of T cell suppression. The binding to PD-1 typically is inhibited by at least 50 percent (e.g., at least 50 percent, 60 percent, 70 percent, 75 percent, 80 percent, 90 percent, 95 percent, or more than 95 percent) as compared to the level of binding in the absence of the fragment. In addition, such fragments can be useful to enhance an immune response, as inhibiting interactions of B7-H1 and B7-DC with PD-1 may also inhibit the suppression of immune responses that would otherwise occur.

Isolated costimulatory polypeptides of the invention can be obtained by, for example, chemical synthesis or by recombinant production in a host cell. To recombinantly produce a costimulatory polypeptide, a nucleic acid containing a nucleotide sequence encoding the polypeptide can be used to transform, transduce, or transfect a bacterial or eukaryotic host cell (e.g., an insect, yeast, or mammalian cell). In general, nucleic acid constructs include a regulatory sequence operably linked to a nucleotide sequence encoding a costimulatory polypeptide. Regulatory sequences (also referred to herein as expression control sequences) typically do not encode a gene product, but instead affect the expression of the nucleic acid sequences to which they are operably linked.

Useful bacterial systems include, for example, *Escherichia coli* strains such as BL-21. An *E. coli* strain can be transformed with a vector such as one of the pGEX series of vectors (Amersham Biosciences Corp., Piscataway, N.J.), which produce fusion proteins containing glutathione S-transferase (GST). Transformed *E. coli* typically are grown exponentially, and then stimulated with isopropylthiogalactopyranoside (IPTG) to induce expression of the polypeptide of interest. The expressed polypeptide may be soluble and easily purified from lysed cells by, for example, adsorption to glutathione-agarose beads followed by elution in the presence of free glutathione. The pGEX vectors are designed to include thrombin or factor Xa protease cleavage sites so that the target gene product can be released from the GST moiety.

In eukaryotic host cells, a number of viral-based expression systems can be utilized to express costimulatory polypeptides (e.g., variant B7-H1 and variant B7-DC polypeptides). A nucleic acid encoding a costimulatory polypeptide of the invention can be cloned into, for example, a baculoviral vector such as pBLUEBAC™ (Invitrogen Life Technologies, Carlsbad, Calif.), which can be used to co-transfect insect cells such as *Spodoptera frugiperda* (Sf9) cells with wild type DNA from *Autographa californica* multiply enveloped nuclear polyhedrosis virus (AcMNPV). Recombinant viruses producing costimulatory polypeptides can be identified by standard methodology. Alternatively, a nucleic acid encoding a costimulatory polypeptide such as variant B7-H1 or variant B7-DC can be introduced into an SV40, retroviral, or vaccinia based viral vector for infection of suitable host cells.

Mammalian cell lines that stably express variant costimulatory polypeptides can be produced using expression vectors with appropriate control elements and a selectable marker. For example, the eukaryotic expression vectors pCR®3.1 (Invitrogen Life Technologies) and p91023(B) (see Wong et al. (1985) *Science* 228:810-815) are suitable for expression of variant costimulatory polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of an expression vector by electroporation, lipofection, calcium phosphate, or calcium chloride co-precipitation, DEAE dextran, or other suitable transfection method, stable cell lines can be selected (e.g., by antibiotic resistance to G418, kanamycin, or hygromycin). The transfected cells can be cultured such that the polypeptide of interest is expressed, and the polypeptide can be recovered from, for example, the cell culture supernatant or from lysed cells. Alternatively, a variant costimulatory polypeptide can be produced by (a) ligating amplified sequences into a mammalian expression vector such as pcDNA™ 3 (Invitrogen Life Technologies), and (b) transcribing and translating in vitro using wheat germ extract or rabbit reticulocyte lysate.

Variant costimulatory polypeptides can be purified using, for example, chromatographic methods such as DEAE ion exchange, gel filtration, and hydroxylapatite chromatography. For example, a costimulatory polypeptide in a cell culture supernatant or a cytoplasmic extract can be purified using a protein G column. In some embodiments, variant costimulatory polypeptides can be "engineered" to contain an amino acid sequence that allows the polypeptides to be captured onto an affinity matrix. For example, a tag such as c-myc, hemagglutinin, polyhistidine, or FLAG™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase. Immunoaffinity chromatography also can be used to purify costimulatory polypeptides.

2. Isolated Nucleic Acid Molecules

The invention provides isolated nucleic acids that include a nucleic acid sequence encoding a costimulatory polypeptide (e.g., a variant B7-H1 or B7-DC polypeptide). As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-B7-H1 or B7-DC proteins). The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

Nucleic acids of the invention can be in sense or antisense orientation, or can be complementary to a reference sequence encoding a costimulatory polypeptide. Reference sequences include, for example, the nucleotide sequences set forth in SEQ ID NOS:7-10 (shown in FIGS. 5-8), which encode full-length, immature costimulatory polypeptides having the amino acid sequences set forth in SEQ ID NOS:3-6, respectively. Nucleic acids of the invention can be DNA, RNA, or nucleic acid analogs. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

Isolated nucleic acid molecules of the invention can be produced by standard techniques, including, without limitation, common molecular cloning and chemical nucleic acid synthesis techniques. For example, polymerase chain reaction (PCR) techniques can be used to obtain an isolated nucleic acid encoding a variant costimulatory polypeptide. PCR is a technique in which target nucleic acids are enzymatically amplified. Typically, sequence information from the ends of the region of interest or beyond can be employed to design oligonucleotide primers that are identical in sequence to opposite strands of the template to be amplified.

PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292-1293.

Isolated nucleic acids of the invention also can be chemically synthesized, either as a single nucleic acid molecule or as a series of oligonucleotides (e.g., using phosphoramidite technology for automated DNA synthesis in the 3' to 5' direction). For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector.

Isolated nucleic acids of the invention also can be obtained by mutagenesis. For example, a reference sequence (e.g., the nucleotide sequence set forth in SEQ ID NO:15, SEQ ID NO:16, SEQ ID NO:17, or SEQ ID NO:18) that encodes a costimulatory polypeptide having an amino acid sequence shown in FIGS. 1-4 (SEQ ID NOs:3-6) can be mutated using standard techniques, including oligonucleotide-directed mutagenesis and/or site-directed mutagenesis through PCR. See, *Short Protocols in Molecular Biology*, Chapter 8, Green Publishing Associates and John Wiley & Sons, edited by Ausubel et al., 1992. Examples of positions that can be modified include those described herein.

3. Vectors and Host Cells

The invention also provides vectors containing nucleic acids such as those described above. As used herein, a "vector" is a replicon, such as a plasmid, phage, or cosmid, into which another DNA segment may be inserted so as to bring about the replication of the inserted segment. The vectors of the invention can be expression vectors. An "expression vector" is a vector that includes one or more expression control sequences, and an "expression control sequence" is a DNA sequence that controls and regulates the transcription and/or translation of another DNA sequence.

In the expression vectors of the invention, the nucleic acid is operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or FLAG™ tag (Kodak, New Haven, Conn.) sequences typically are expressed as a fusion with the encoded polypeptide. Such tags can be inserted anywhere within the polypeptide including at either the carboxyl or amino terminus.

The invention also provides host cells containing vectors of the invention. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Suitable methods for transforming and transfecting host cells are found in Sambrook et al., *Molecular Cloning: A Laboratory Manual* ($2^{nd}$ edition), Cold Spring Harbor Laboratory, New York (1989), and reagents for transformation and/or transfection are commercially available [e.g., Lipofectin (Invitrogen Life Technologies); Fugene (Roche, Indianapolis, Ind.); and SuperFect (Qiagen, Valencia, Calif.)]. A host cell (e.g., a prokaryotic cell or a eukaryotic cell such as a COS cell) can be used to, for example, produce the costimulatory polypeptides provided herein. In some embodiments, a host cell (e.g., an APC) can be used to express the costimulatory polypeptides of the invention for presentation to a T cell.

4. Methods

The invention provides methods that include using variant costimulatory polypeptides to enhance T cell responses. The costimulatory molecules B7-H1 and B7-DC can bind to PD-1 (programmed cell death-1), a CD28 homolog with an immunoreceptor tyrosine-based inhibitory motif in its cytoplasmic domain (Ishida et al. (1992) *EMBO J.* 11:3887-3895). PD-1 is expressed on a subset of thymocytes and is up-regulated on T cells, B cells, and myeloid cells after their activation (Agata et al. (1996) *Int. Immunol.* 8:765-772).

PD-1 appears to be a negative regulator of immune responses in vivo. For example, PD-1$^{-/-}$ mice in the C57BL/6 background slowly developed a lupus-like glomerulonephritis and progressive arthritis (Nishimura et al. (1999) *Immunity* 11:141-151). Additionally, PD-1$^{-/-}$ mice in the BALB/c background rapidly developed a fatal autoimmune dilated cardiomyopathy (Nishimura et al. (2001) *Science* 291:319-322). Evidence also indicates, however, that both B7-H1 and B7-DC can function to costimulate a T cell response. In the presence of suboptimal TCR signals, B7-H1 or B7-DC can stimulate increased proliferation and production of cytokines in vitro. In addition, infusion of a B7-H1Ig fusion polypeptide can increase CD4$^+$ T cell responses and Th-dependent humoral immunity. Thus, B7-H1 and B7-DC may also bind to T cell receptors other than PD-1. Indeed, it has been shown that B7-H1 expressed on tumor cells can actively inhibit immune responses by promoting the apoptosis of effector CTLs, and the apoptotic effect of B7-H1 is mediated largely by receptors other than PD-1 (Dong et al. (2002) *Nature Med.* 8:793-800).

The experiments described in the Examples below indicate that the costimulatory activity of B7-H1 and B7-DC, and the described variants of each, is not mediated by the PD-1 receptor. Thus, the invention provides methods for using a variant costimulatory polypeptide with reduced affinity for PD-1 to stimulate a T cell response. The methods can include contacting a T cell with a purified variant costimulatory polypeptide. The contacting can be in vitro, ex vivo, or in vivo (e.g., in a mammal such as a mouse, rat, rabbit, dog, cow, pig, non-human primate, or a human).

The contacting can occur before, during, or after activation of the T cell. Typically, contacting of the T cell with variant costimulatory polypeptide can be at substantially the same time as activation. Activation can be, for example, by exposing the T cell to an antibody that binds to the T cell receptor (TCR) or one of the polypeptides of the CD3 complex that is physically associated with the TCR. Alternatively, a T cell can be exposed to either an alloantigen (e.g., a MHC alloantigen) on, for example, an APC [e.g., an interdigitating dendritic cell (referred to herein as a dendritic cell), a macrophage, a monocyte, or a B cell] or an antigenic peptide produced by processing of a protein antigen by any of the above APC and presented to the T cell by MHC molecules on the surface of the APC. The T cell can be a $CD4^+$ T-cell or a $CD8^+$ T cell.

In some embodiments, a purified variant costimulatory polypeptide can be administered directly to a T cell. Alternatively, an APC such as a macrophage, monocyte, interdigitating dendritic cell (referred to herein as a dendritic cell), or B cell can be transformed, transduced, or transfected with a nucleic acid containing a nucleotide sequence that encodes a variant costimulatory polypeptide, and the T cell can be contacted by the transformed, transduced, or transfected APC. The transformed, transduced, or transfected cell can be a cell, or a progeny of a cell that, prior to being transformed, transduced, or transfected, was obtained from the subject to which it is administered, or from another subject (e.g., another subject of the same species).

The variant costimulatory polypeptide can be any of those described herein. For example, a B7-H1 polypeptide can contain a substitution at position 67, position 126, position 37, position 115, or position 124 (e.g., an alanine substitution for phenylalanine at position 67, an alanine substitution for isoleucine as position 126, a tyrosine substitution for threonine at position 37, an alanine substitution for isoleucine at position 115, or a serine substitution for lysine at position 124), each with respect to SEQ ID NO:4. Alternatively, the variant costimulatory polypeptide can be, for example, a B7-DC polypeptide containing a substitution at position 111, 113, 56, 67, 71, 101, or 105 (e.g., a serine substitution for aspartic acid at position 111, a serine substitution for lysine at position 113, a serine substitution for arginine at position 56, a tyrosine substitution for serine at position 67, a serine substitution for glutamic acid at position 71, a serine substitution for arginine at position 101, or an alanine substitution for isoleucine at position 105), each with respect to SEQ ID NO:6.

If the activation is in vitro, the variant B7-H1 molecule or variant B7-DC molecule can be bound to the floor of a the relevant culture vessel, e.g. a well of a plastic microtiter plate.

In vitro application of the purified variant costimulatory polypeptides can be useful, for example, in basic scientific studies of immune mechanisms or for production of activated T cells for use in studies of T cell function or, for example, passive immunotherapy. Furthermore, variant B7-H1 and variant B7-DC polypeptides can be added to in vitro assays (e.g., T cell proliferation assays) designed to test for immunity to an antigen of interest in a subject from which the T cells were obtained. Addition of variant costimulatory polypeptides to such assays would be expected to result in a more potent, and therefore more readily detectable, in vitro response. Moreover, a variant B7-H1 or B7-DC polypeptide, or an APC transformed, transfected, or transduced with a nucleic acid encoding such a polypeptide, can be used: (a) as a positive control in an assay to test for co-stimulatory activity in other molecules; or (b) in screening assays for compounds useful in inhibiting T costimulation (e.g., compounds potentially useful for treating autoimmune diseases or organ graft rejection).

The variant B7-H1 and variant B7-DC polypeptides provided herein are generally useful as in vivo and ex vivo as immune response-stimulating therapeutics. For example, the polypeptides of the invention can be used for treatment of disease conditions characterized by immunosuppression, such as, without limitation, cancer, AIDS or AIDS-related complex, other virally or environmentally-induced conditions, and certain congenital immune deficiencies. The polypeptides also can be employed to increase immune function that has been impaired by the use of radiotherapy of immunosuppressive drugs (e.g., certain chemotherapeutic agents), and therefore can be particularly useful when given in conjunction with such drugs or radiotherapy. In addition, variant B7-H 1 molecules can be used to treat conditions involving cellular immune responses, including, for example, inflammatory conditions (e.g., conditions induced by infectious agents such as *Mycobacterium tuberculosis* or *M. leprae*), or other pathologic cell-mediated responses such as those involved in autoimmune diseases (e.g., rheumatoid arthritis, multiple sclerosis, or insulin-dependent diabetes mellitus).

Methods of the invention can be applied to a wide range of species, e.g., humans, non-human primates, horses, cattle, pigs, sheep, goats, dogs, cats, rabbits, guinea pigs, hamsters, rats, and mice.

In some in vivo approaches, a variant B7-H1 or variant B7-DC polypeptide (or a functional fragment thereof) itself is administered to a subject in a therapeutically effective amount. Typically, polypeptides of the invention can be suspended in a pharmaceutically-acceptable carrier. Pharmaceutically acceptable carriers are biologically compatible vehicles (e.g., physiological saline) that are suitable for administration to a human. A therapeutically effective amount is an amount of a variant costimulatory polypeptide that is capable of producing a medically desirable result (e.g., an enhanced T cell response) in a treated animal. Variant costimulatory polypeptides can be administered orally or by intravenous infusion, or injected subcutaneously, intramuscularly, intraperitoneally, intrarectally, intravaginally, intranasally, intragastrically, intratracheally, or intrapulmonarily. The variant costimulatory polypeptides can be delivered directly to an appropriate lymphoid tissue (e.g., spleen, lymph node, or mucosal-associated lymphoid tissue). The dosage required typically depends on the choice of the route of administration, the nature of the formulation, the nature of the subject's illness, the subject's size, weight, surface area, age, and sex, other drugs being administered, and the judgment of the attending physician. Suitable dosages typically are in the range of 0.01-100.0 µg/kg. Wide variations in the needed dosage are to be expected in view of the variety of polypeptides and fragments available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2- or 3-, 4-, 6-, 8-, 10-, 20-, 50-, 100-, 150-, or more fold). Encapsulation of a purified variant costimulatory polypeptide in a suitable delivery vehicle (e.g., polymeric microparticles or implantable devices) may increase the efficiency of delivery, particularly for oral delivery.

Alternatively, a nucleic acid containing a nucleotide sequence encoding a variant B7-H1 or B7-DC polypeptide or functional fragment thereof can be delivered to an appropriate cell of an animal. Expression of the coding sequence typically is directed to lymphoid tissue of the subject by, for example, delivery of the nucleic acid to the lymphoid tissue. This can be achieved by, for example, using a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 μm in diameter can be used. The nucleic acid can be encapsulated in these microparticles, which are taken up by macrophages and gradually biodegraded within the cell, thereby releasing the nucleic acid. Once released, the nucleic acid can be expressed within the cell. A second type of microparticle that also can be useful is intended not to be taken up directly by cells, but rather to serve primarily as a slow-release reservoir of nucleic acid. The nucleic acid is taken up by cells only upon release from the microparticle through biodegradation. Such polymeric particles typically are large enough to preclude phagocytosis (i.e., larger than 5 μm, and typically larger than 20 μm).

Another way to achieve uptake of a nucleic acid is to use liposomes, which can be prepared by standard methods known in the art, for example. Nucleic acid vectors can be incorporated alone into these delivery vehicles or can be co-incorporated with tissue-specific antibodies. Alternatively, a molecular conjugate can be prepared to contain a plasmid or other vector attached to poly-L-lysine by electrostatic or covalent forces. Poly-L-lysine binds to a ligand that can bind to a receptor on target cells (Cristiano et al. (1995) *J. Mol. Med.* 73:479-486). Alternatively, lymphoid tissue specific targeting can be achieved using lymphoid tissue-specific transcriptional regulatory elements (TREs) such as a B lymphocyte-, T lymphocyte-, or dendritic cell-specific TRE. Lymphoid tissue specific TREs include, for example, those known in the art [see, e.g., Thompson et al. (1992) *Mol. Cell. Biol.* 12:1043-1053; Todd et al. (1993) *J. Exp. Med.* 177: 1663-1674; and Penix et al. (1993) *J. Exp. Med.* 178:1483-1496]. Delivery of "naked DNA" (i.e., without a delivery vehicle) to an intramuscular, intradermal, or subcutaneous site is another means to achieve in vivo expression.

For in vivo expression of the variant costimulatory polypeptides provided herein, short amino acid sequences can act as signals to direct the polypeptides to specific intracellular compartments. For example, hydrophobic signal peptides having amino acid sequences such as MAISGVPVLGFFIIAVLMSAQESWA (SEQ ID NO:19) are found at the amino terminus of proteins destined for the ER. In addition, amino acid sequences such as KFERQ (SEQ ID NO:20) and other closely related sequences can target intracellular polypeptides to lysosomes, while amino acid sequences such as, for example, MDDQRDLISNNEQLP (SEQ ID NO:21) can direct polypeptides to endosomes. In addition, the amino acid sequence KDEL (SEQ ID NO:22) can act as a retention signal for the ER. Each of these signal peptides, or a combination thereof, can be used to traffic the variant B7-H1 and variant B7-DC polypeptides of the invention to specific cellular compartments. DNAs encoding the variant B7-H1 and B7-DC polypeptides containing targeting signals can be generated by, for example, PCR or other standard genetic engineering or synthetic techniques.

Similar to polypeptides, a therapeutic amount of a nucleic acid can be administered in a pharmaceutically acceptable carrier such as, for example, physiological saline. A therapeutically effective amount of a nucleic acid is an amount of the nucleic acid that is capable of producing a medically desirable result (e.g., an enhanced T cell response) in a treated animal. As described above, dosages will vary. Typical dosages for administration of nucleic acids are from approximately $10^6$ to $10^{12}$ copies of the nucleic acid molecule. This dose can be repeatedly administered, as needed. Routes of administration can be any of those listed above.

Ex vivo methods can include, for example, the steps of harvesting cells from a subject, culturing the cells, transducing them with an expression vector, and maintaining the cells under conditions suitable for expression of the variant costimulatory polypeptides provided herein. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject.

In some ex vivo methods, peripheral blood mononuclear cells (PBMC) can be withdrawn from a patient or a suitable donor and exposed ex vivo to an activating stimulus (see above) and a variant costimulatory polypeptide (whether in soluble form or attached to a sold support by standard methodologies). The PBMC containing highly activated T cells then can be introduced into the same or a different patient.

An alternative ex vivo strategy can involve transfecting or transducing cells obtained from a subject with a nucleic acid encoding a variant B7-H1 or B7-DC polypeptide. The transfected or transduced cells then can be returned to the subject. While such cells typically would be hemopoietic cells (e.g., bone marrow cells, macrophages, monocytes, dendritic cells, or B cells), they can also be any of a wide range of types including, without limitation, fibroblasts, epithelial cells, endothelial cells, keratinocytes, or muscle cells in which they act as a source of the variant B7-H1 or B7-DC polypeptide for as long as they survive in the subject. The use of hemopoietic cells, including the above APC, can be particularly useful, as such cells typically are expected to home to, among others, lymphoid tissue (e.g., lymph nodes or spleen) and thus the variant B7-H1 or B7-DC polypeptide can be produced in high concentration at the site where its effect (i.e., enhancement of an immune response) is exerted. In addition, if APC are used, the APC expressing the exogenous variant costimulatory molecule can be the same APC that present an alloantigen or antigenic peptide to the relevant T cell. The variant B7-H1 or variant B7-DC can be secreted by the APC or expressed on its surface.

Methods for inhibiting interactions of B7-H1 or B7-DC with PD-1 also are provided herein. These methods can include contacting a PD-1 polypeptide with a fragment of B7-H1 or B7-DC. The fragment can contain, for example, amino acids 67-69 of B7-H1, amino acids 113-115 of B7-H1, or amino acids 124-126 of B7-H1, each with respect to SEQ ID NO:4. Alternatively, the fragment can contain, for example, amino acids 67-71 of B7-DC, amino acids 101-105 of B7-DC, or amino acids 111-113 of B7-DC, each with respect to SEQ ID NO:6.

The PD-1 polypeptide can be contacted in vitro or in vivo (e.g., in a mammal such as a mouse, rat, rabbit, dog, cow, non-human primate, or human). The polypeptide fragment can be administered directly, or the method can include administering to a mammal a nucleic acid containing a nucleotide sequence encoding the polypeptide fragment. In some embodiments, the method can include administering to a mammal a cell, or the progeny of a cell, that has been transformed, transduced, or transfected with a nucleic acid encoding the polypeptide fragment. The cell can be a cell, or a progeny of a cell that, prior to being transformed, transduced, or transfected, was obtained from the mammal to which the cell is administered.

5. Articles of Manufacture

The invention also provides articles of manufacture that can contain the variant costimulatory polypeptides, functional fragments of costimulatory polypeptides, and/or inhibitory fragments of costimulatory polypeptides provided herein. Articles of manufacture also can include the nucleic acids and host cells provided herein. For example, an article of manufacture can include a variant B7-H1 or B7-DC polypeptide, or a nucleic acid encoding a variant B7-H1 or variant B7-DC polypeptide, packaged in a container (e.g., a vial). In addition, such an article of manufacture can include a label or instructions indicating that the polypeptide or nucleic acid can be used to enhance T cell activation. Alternatively, an article of manufacture can include a fragment of a B7-H1 or B7-DC polypeptide packaged in a container, and also can include a label or instructions indicating that the fragment can be used to inhibit binding to PD-1.

The invention will be further described in the following examples, which do not limit the scope of the invention described in the claims.

EXAMPLES

Example 1

Materials and Methods

Mice and Cell lines: Female C57BL/6 (B6) mice were purchased from the National Cancer Institute (Frederick, Md.). PD-1-deficient (PD-1$^{-/-}$) mice were generated as described previously (Nishimura et al. (1998) *Int. Immunol.* 10:1563-1572). Stably transfected Chinese hamster ovary (CHO) cell clones secreting fusion proteins were maintained in CHO-SF II medium (Invitrogen Life Technologies) supplemented with 1% dialyzed fetal bovine serum (FBS; HyClone, Logan, Utah). Lymphocytes and COS cells were grown in Dulbecco's modified Eagle medium (DMEM; Invitrogen Life Technologies) supplemented with 10% FBS, 25 mM HEPES, 2 mM L-glutamine, 1 mM sodium pyruvate, 1% MEM nonessential amino acids, 100 U/ml penicillin G, and 100 µg/ml streptomycin sulfate.

Ig Fusion Proteins: Fusion proteins containing the extracellular domain of mouse PD-1 linked to the Fc portion of mouse IgG2a (PD-1Ig) were produced in stably transfected CHO cells and purified by protein G affinity column as described previously (Wand et al. supra). Total RNA was isolated from mouse spleen cells and B7-DC cDNA was obtained by reverse-transcription PCR. B7-H1Ig and B7-DCIg were prepared by transiently transfecting COS cells with a plasmid containing a chimeric cDNA that included the extracellular domain of mouse B7-H1 (Tamura et al. supra) or B7-DC linked in frame to the CH2-CH3 portion of human IgG1. The transfected COS cells were cultured in serum-free DMEM, and concentrated supernatants were used as sources of Ig fusion proteins for initial binding assays. The Ig proteins were further purified on a protein G column for BIAcore analysis and functional assays as described previously (Wand et al. supra).

Molecular modeling: Molecular models of the Ig V-type domains of human B7-H1 (hB7-H1), mouse B7-H1 (mB7-H1), human B7-DC (hB7-DC), and mouse B7-DC (mB7-DC) were generated by homology (or comparative) modeling based on X-ray coordinates of human CD80 and CD86, as seen in the structures of the CD80/CTLA-4 and CD86/CTLA-4 complexes. First, the V-domains of CD80 and CD86 were optimally superimposed, and sequences of B7 family members were aligned based on this superimposition. The superimposition and initial alignments were carried out using the sequence-structure alignment function of MOE (Molecular Operating Environment, Chemical Computing Group, Montreal, Quebec, Canada). The alignment was then manually adjusted to match Ig consensus positions and to map other conserved hydrophobic residues in the target sequences to core positions in the X-ray structures. Corresponding residues in the aligned sequences thus were predicted to have roughly equivalent spatial positions. Taking this kind of structural information into account typically is a more reliable alignment criterion than sequence identity alone if the identity is low, as in this case. In the aligned region, the average identity of the compared B7 sequences relative to the two structural templates, CD80 and CD86, was only approximately 16%. The final version of the structure-oriented sequence alignment, which provided the basis for model building, is shown in FIG. 9. Following the alignment, core regions of the four models were automatically assembled with MOE from the structural templates, and insertions and deletions in loop regions were modeled by applying a segment matching procedure (Levitt (1992) *J. Mol. Biol.* 226: 507-533; and Fechteler et al. (1995) *J. Mol. Biol.* 253:114-131). Side chain replacements were carried out using preferred rotamer conformations seen in high-resolution protein databank structures (Ponder and Richards (1987) *J. Mol. Biol.* 193:775-791; and Berman et al. (2000) *Nucl. Acids Res.* 28:235-242). In each case, twenty intermediate models were generated, average coordinates were calculated, and the resulting structures were energy minimized using a protein force field (Engh and Huber (1991) *Acta Cryst. A*47:392-400) until intramolecular contacts and stereochemistry of each model were reasonable. Graphical analysis of the models, including calculation of solvent-accessible surfaces (Connolly (1983) *J. Appl. Cryst.* 16:548-558) and residue mapping studies were carried out with INSIGHTII® (Accelrys, San Diego, Calif.).

Site-directed Mutagenesis: All mutants of B7-H1Ig and B7-DCIg were constructed using a two-step PCR technique, in which B7-H1Ig and B7-DCIg cDNAs, respectively, were used as templates. Overlapping oligonucleotide primers were synthesized to encode the desired mutations, and two flanking 5' and 3' primers were designed to contain EcoR I and Bgl II restriction sites, respectively. Appropriate regions of the cDNAs initially were amplified using the corresponding overlapping and flanking primers. Using the flanking 5' and 3' primers, fragments with overlapping sequences were fused together and amplified. PCR products were digested with EcoR I and Bgl II and ligated into EcoR I/Bgl II-digested pHIg vectors. To verify that the desired mutations were introduced, each mutant was sequenced using an ABI Prism 310 Genetic Analyzer. Plasmids were transfected into COS cells, and serum-free supernatants were harvested and used for in vitro binding assays or purified on a protein G column for BIAcore analysis and functional assays.

ELISA: A sandwich ELISA specific for B7-H1Ig and B7-DCIg was established as described previously. Briefly, microtiter plates were coated with 2 µg/ml goat anti-human IgG (Sigma, St. Louis, Mo.) overnight at 4° C. Wells were blocked for 1 hour with blocking buffer (10% FBS in PBS) and washed with PBS containing 0.05% Tween 20 (PBS-Tween). COS cell culture supernatants were added and incubated for 2 hours at room temperature. Known concentrations of purified B7-H1Ig also were added to separate wells on each plate for generation of a standard curve. After extensive washing, horseradish peroxidase (HRP)-conjugated goat anti-human IgG (TAGO, Inc., Burlingame, Calif.) diluted 1:2000 was added and subsequently developed with TMB substrate before stopping the reaction by the addition of 0.5 M $H_2SO_4$. Absorbance was measured at 405 nm on a microtiter plate reader. Concentrations of mutant fusion proteins were determined by comparison with the linear range of a standard curve of B7-H1Ig. Data from triplicate wells were collected, and the standard deviations from the mean were <10%. Experiments were repeated at least three times.

The ability of mutant and wild type B7-H1Ig and B7-DCIg fusion polypeptides to bind PD-1 was measured using a capture ELISA assay. Recombinant PD-1Ig fusion proteins were coated on microtiter plates at 5 µg/ml overnight at 4° C. The plates were blocked and washed, and COS cell culture media was added and incubated for 2 hours at room temperature. After extensive washing, HRP-conjugated goat anti-human IgG was added, followed by TMB substrate and measurement of absorbance at 405 nm.

Flow Cytometry: Human embryonal kidney 293 cells were transfected with a PD-1 GFP vector, which was constructed by fusing GFP (green fluorescent protein cDNA) in frame to the C terminal end of a full-length mouse PD-1 cDNA. The cells were harvested 24 hours after transfection and incubated in FACS (fluorescence activated cell sorting) buffer (PBS, 3% FBS, 0.02% $NaN_3$) with equal amounts of fusion proteins, which had been titrated using wild type B7-H1Ig and B7-DCIg, in COS cell culture media on ice for 45 minutes. An unrelated fusion protein containing human Ig was used as a negative control. The cells were washed, further incubated with fluorescein isothiocyanate (PE)-conjugated goat anti-human IgG (BioSource, Camarillo, Calif.), and analyzed on a FACScaliber (Becton Dickinson, Mountain View, Calif.) with Cell Quest software (Becton Dickinson). GFP-positive cells were gated by FL1.

Surface Plasmon Resonance Analysis: The affinity of purified wild type and mutant B7-H1 and B7-DC polypeptides was analyzed on a BIACORE™ 3000 instrument (Biacore AB, Uppsala, Sweden). All reagents except fusion proteins were purchased, pre-filtered, and degassed from BIAcore. All experiments were performed at 25° C. using 0.1 M HEPES, 0.15 M NaCl (pH 7.4) as a running buffer. Briefly, PD-1Ig was first immobilized onto a CM5 sensor chip (BIAcore) by amine coupling according to the BIAcore protocol. A flow cell of the CM5 chip was derivatized through injection of a 1:1 EDC:NHS [N-ethyl-N'(diethylaminopropyl) carbodiimide:N-hydroxysuccinimide] mixture for seven minutes, followed by injection of 20 µg/ml of PD-1Ig at 10 µl/min diluted in 10 mM sodium acetate (pH 4.5). The PD-1Ig was immobilized at 2000 RUs. This was followed by blocking the remaining activated carboxyl groups with 1 M ethanolamine (pH 8.5). A control flow cell was prepared in a similar fashion as above, substituting running buffer alone in place of PD-1Ig. The fusion proteins were diluted in running buffer in a concentration series of 3.75, 7.5, 15, 30, and 60 µg/ml. The proteins were injected at a flow rate of 20 µl/min for 3 minutes, and buffer was allowed to flow over the surface for 5 minutes for dissociation data. The flow cells were regenerated with a single 30-second pulse of 10 mM NaOH. Data analysis was performed using BIAevaluation software package 3.1 (BIAcore).

T cell proliferation and cytokine assays: T cells from wild type B6 mice or PD-1$^{-/-}$ mice were purified using nylon wool columns (Robbins Scientific Co, Sunnyvale, Calif.) as described previously (Wang et al. supra). The enriched T cells were cultured at 3×10$^5$ cells per well in flat-bottomed 96-well microplates that were pre-coated with anti-CD3 mAb (clone 145-2C11, Pharmingen, San Diego, Calif.) in the presence of 5 µg/ml of fusion or control polypeptides. Proliferation of T cells was determined by incorporation of 1 µCi/well $^3$H-TdR during the last 12 hours of the 3-day culture. $^3$H-TdR incorporation was counted using a MICROBETA® Trilux liquid scintillation counter (Wallac, Finland). To detect cytokine, culture supernatants were collected at various time points, and the concentration of IFN-γ was measured by sandwich ELISA following the manufacturer's instructions (Pharmngen).

Example 2

Sequences, Structures, and Molecular Models

The V-regions in CD80 and CD86 share only limited sequence identity (approximately 20%), but their three-dimensional structures are very similar as revealed by independent crystallographic studies. Many core or Ig superfamily consensus residue positions seen in CD80/CD86 also are conserved or conservatively replaced in other B7 family members, including B7-H1 and B7-DC (FIG. 9).

Molecular models of mouse and human B7-H1 and B7-DC molecules were constructed. These models revealed that in the V-regions, B7-H1 and B7-DC share more sequence identity than average across the B7 family—approximately 34%. Since both B7-H1 and B7-DC bind PD-1, residue conservation could be significant for formation of the receptor binding structure. Therefore, the models were used to compare the putative distribution of conserved residues that are exposed on the protein surface. A side-by-side comparison of these molecular models revealed significant conservation of surface residues on the BED faces of B7-H1 and B7-DC, more so in the human than the mouse proteins. In contrast, the opposite A'GFCC'C" faces did not display significant residue conservation. This result was somewhat unexpected because the corresponding A'GFCC'C" faces of both CD80 and CD86 contain the CD28/CTLA-4 binding sites.

Example 3

Mutagenesis Analysis of Receptor Binding Sites

With the aid of the molecular models, the V-domains of B7-H1 and B7-DC were scanned for important residues. Conserved and non-conserved residues on both the BED and A'GFCC'C" faces were selected for site-specific mutagenesis. Residues in the mouse molecules were mutated to enable subsequent functional studies of selected mutant proteins. The binding characteristics of the resulting mutant proteins were assessed by specific ELISA and FACS analysis for binding to PD-1. A total of 21 mB7-H1 and 17 mB7-DC mutants were prepared and tested. The results are summarized in Tables 1 and 2. Particular residues within mB7-H1 and mB7-DC were only considered to be important for ligand-receptor interactions if their mutation caused at least a 50% loss of binding by FACS, or at least an order of magnitude loss by ELISA.

Mutation of about half of these residues significantly abolished binding to mPD-1. In particular, mB7-H1 residues F67, I115, K124, and I126 were identified as important for binding to mPD1. For mB7-DC, the identified residues were E71, I105, D111, and K113. All of these important residues are located in the C', C", F, and G strands of the A'GFCC'C" face, but not in the BED face. Mutation of three residues in mB7-H1 (E58, A69, and C113) increased binding to mPD-1 three- to four-fold as determined by ELISA. Thus, these positions must at least be proximal to the receptor-ligand interface and have not only some tolerance for substitution but also potential optimization of binding interactions.

TABLE 1

Summary of amino acid substitutions and binding characteristics of mouse B7-H1 mutants

| | | | | Binding activity | |
|---|---|---|---|---|---|
| Mu- | | Substitutions[b] | | | ELISA |
| tants[a] | Sites | Nucleic acid | Amino acid | FACS | (%)[c] |
| B7-H1 | | | | ++++ | 100 |
| L27A | A' strand | TTG > GCC | Leu > Ala | ++++ | 100 |
| E31S | A' strand | GAG > AGC | Glu > Ser | ++ | 50 |
| S34Y | B strand | AGC > TAC | Ser > Tyr | ++++ | 60 |
| T37Y | B strand | ACG > TAC | Thr > Tyr | ++ | 5 |
| D49S | B/C strand | GAC > AGC | Asp > Ser | ++++ | 30 |
| Y56S | C strand | TAC > AGC | Tyr > Ser | ++++ | 100 |
| E58S | C strand | GAA > AGC | Glu > Ser | +++++ | 300 |
| E62S | C/C' strand | GAG > AGC | Glu > Ser | ++++ | 50 |
| F67A | C' strand | TTT > GCC | Phe > Ala | +/− | 2 |
| A69F | C' strand | GCA > TTC | Ala > Phe | +++++ | 300 |
| E72S | C' strand | GAG > AGC | Glu > Ser | ++++ | 60 |
| K75S | C"/D strand | AAG > AGC | Lys > Ser | ++++ | 100 |
| K89S | D strand | AAG > AGC | Lys > Ser | ++++ | 60 |
| A98F | E strand | GCC > TTC | Ala > Phe | ++++ | 40 |
| Q100S | E strand | CAG > AGC | Gln > Ser | ++++ | 100 |
| C113Y | F strand | TGC > TAC | Cys > Tyr | +++++ | 300 |
| I115A | F strand | ATA > GCC | Ile > Ala | +/− | 3 |
| S117Y | F strand | AGC > TAC | Ser > Tyr | ++++ | 100 |
| K124S | G strand | AAG > AGC | Lys > Ser | + | 3 |
| I126A | G strand | ATC > GCC | Ile > Ala | − | 1.4 |
| K129S | G strand | AAA > AGC | Lys > Ser | ++ | 35 |

[a]Amino acids are numbered from the initiator methionine.
[b]Nucleotides or amino acids in front of the slash were replaced with the corresponding nucleotides or amino acids after the slash.
[c]Specific binding activities were determined for each of the indicated fusion proteins.

The concentration of a fusion protein required to give an arbitrary $A_{405}$ the same as that found for wild type B7-H1Ig was determined from the linear region of binding curves and expressed as a percentage of specific binding activity of B7-H1Ig. Values represent the average of three determinations from each binding curve, and are representative of four experiments.

TABLE 2

Summary of amino acid substitutions and binding characteristics of mouse B7-DC mutants

| | | | | Binding activity | |
|---|---|---|---|---|---|
| Mu- | | Substitutions[b] | | | ELISA |
| tants[a] | Sites | Nucleic acid | Amino acid | FACS | (%)[c] |
| B7-DC | | | | ++++ | 100 |
| D33S | A' strand | GAC > AGC | Asp > Ser | ++++ | 30 |
| S39Y | B strand | AGC > TAC | Ser > Tyr | ++++ | 60 |
| E41S | B strand | GAG > AGC | Glu > Ser | ++++ | 100 |
| R56S | C strand | AGA > TCT | Arg > Ser | +++/++ | 5 |
| S58Y | C strand | AGT > TAC | Ser > Tyr | ++++ | 170 |
| D65S | C' strand | GAT > AGC | Asp > Ser | ++++ | 100 |
| S67Y | C' strand | TCT > TAC | Ser > Tyr | +++/++ | 3 |
| E71S | C" strand | GAA > AGC | Glu > Ser | +++/++ | 2 |
| R72S | C" strand | AGA > AGC | Arg > Ser | ++++ | 60 |
| K84S | D strand | AAG > AGC | Lys > Ser | +++/++++ | 13 |
| H88A | E strand | CAC > GCC | His > Ala | +++/++++ | 20 |
| R101S | F strand | CGT > AGC | Arg > Ser | +++ | 7 |
| L103A | F strand | CTG > GCC | Leu > Ala | +++ | 25 |
| I105A | F strand | ATC > GCC | Ile > Ala | ++ | 0.5 |
| D111S | G strand | GAC > AGC | Glu > Ser | ++ | 0.3 |
| K113S | G strand | AAG > AGC | Lys > Ser | +/− | <0.1 |
| T116Y | G strand | ACG > TAC | Thr > Tyr | +++/++++ | 20 |

[a]Amino acids are numbered from the initiation methionine.
[b]The nucleotides or amino acids in front of the slash were replaced with the corresponding nucleotides or amino acids after the slash.
[c]Specific binding activities were determined for each of the indicated fusion proteins.

The concentration of a fusion protein required to give an arbitrary $A_{405}$ the same as that found for wild type B7-DCIg was determined from the linear region of binding curves and expressed as a percentage of specific binding activity of B7-DCIg. Values represent the average of three determinations from each binding curve, and are representative of four experiments.

Residues in mB7-H1 and mB7-DC that significantly reduced or abolished PD-1 when mutated were clustered in equivalent regions of the A'GFCC'C" face of the domains (with one exception in each case), although they often were distant in sequence. In contrast, mutation of conserved residues on the BED face did not reduce binding. Thus, residue conservation on the BED face may be important for other effects such as ligand dimerization or recognition of other proteins.

The PD-1 binding sites mapped to equivalent regions on the opposite A'GFCC'C" face. Mapping of the binding site regions revealed that residues whose mutation negatively (or positively) affected PD-1 binding could form coherent surfaces in both ligands. The proximity of important residues and some residues not important for binding again suggested that the observed effects were specific, and were not a consequence of global structural changes. This was further supported by the ability to produce higher avidity mutants of mB7-H1. Comparison of important residue positions confirmed that the location of the putative binding sites in mB7-H1 and mB7-DC closely corresponded to the CD28/CTLA-4 binding sites in CD86 and CD80.

Figure 10B:
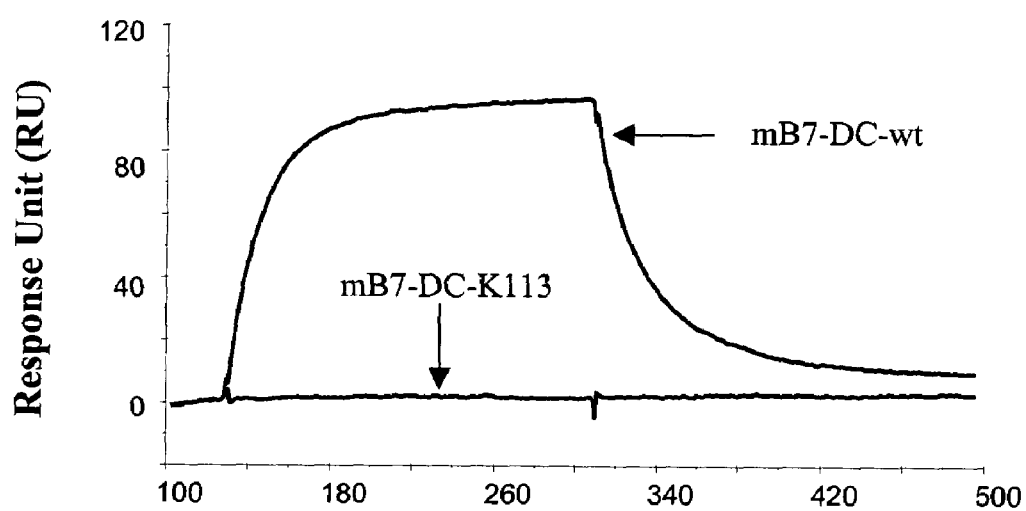

Surface plasmon resonance analysis of binding of wild type and mutant proteins to PD-1 was largely consistent with the results from the FACS and ELISA analyses. The B7-H1 mutant C113 had a similar or slightly higher maximal response (Rmax) value than the wild type protein (321 resonance units (RU) vs. 291 RU), while the mutant I126 (56.1 RU) showed relatively minimal binding to mPD-1 (FIG. 10A). The wild type B7-DC protein had an Rmax of 227 RU, and the B7-DC mutant K113 did not bind to PD-1 at all (FIG. 10B). These data demonstrated that wild type B7-H1 and mutant C113 had a greater steady state affinity for PD-1 than mutant I126, similar to wild type B7-DC as compared to mutant K113. The B7-H1 mutant C113, wild type B7-H1, and wild type B7-DC all had similar on-rates and off-rates, while only the mutants I126 and K113 showed slower or no on- and off-rates, respectively.

Example 4

Costimulatory Function of B7-H1 and B7-DC Mutants

Figure 11A:
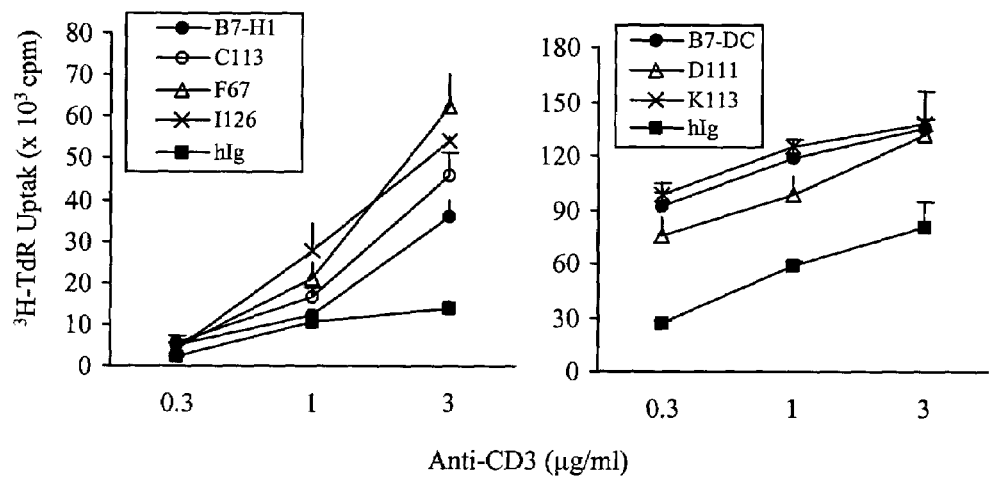
FIGS. 11A and 11B are graphs showing effects of wild type and mutant B7-DC and B7-H1 molecules on T-cell costimulation. Data in FIG. 11A represent T cell proliferation after stimulation with the indicated wild type or mutant B7-H1 and B7-DC Ig fusion proteins in the presence of anti-CD3 mAb coated onto the well-bottoms of 96-well plates at the indicated concentrations. T cell proliferation was measured as incorporation of $^3$H-Thymidine (3H-TdR). Human Ig (hIg) was used as a negative control for the costimulatory molecules. Data depict one representative experiment of three. Data in FIG. 11B represent IFN-γ secretion by T cells cultured in the presence of the indicated Ig fusion proteins and anti-CD3 for 48 or 72 hours. Data depict one representative experiment of three.
Figure 11B:
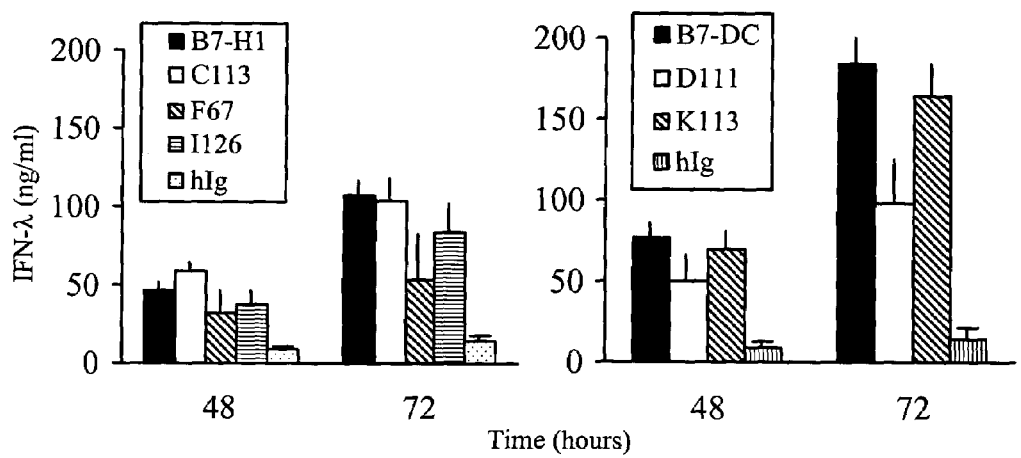

The costimulatory potential of selected mutants also was tested. B7-H1 mutants F67 and I126, and B7-DC mutants K113 and D11 were selected for analysis. Both F67 and I126 had minimal binding to PD-1 in both FACS and ELISA assays (Table 1). Similarly, K113 and D11 did not bind PD-1 (Table 2). As shown in FIGS. 11A and 11B, these mutants were still able to costimulate T cell proliferation and IFN-γ production in comparison with wild type B7-H1 and B7-DC. In fact, B7-H1 mutants F67 and I126 had even slightly increased costimulatory ability as compared to wild type B7-H1. Interestingly, mutant C113, which had approximately 3-fold increased binding capacity to PD-1 as compared to wild type B7-H1 (Table 1), also costimulated T cell proliferation and IFN-γ production. These results indicate that PD-1 is not a costimulatory receptor for B7-H1 and B7-DC.

Figure 12:
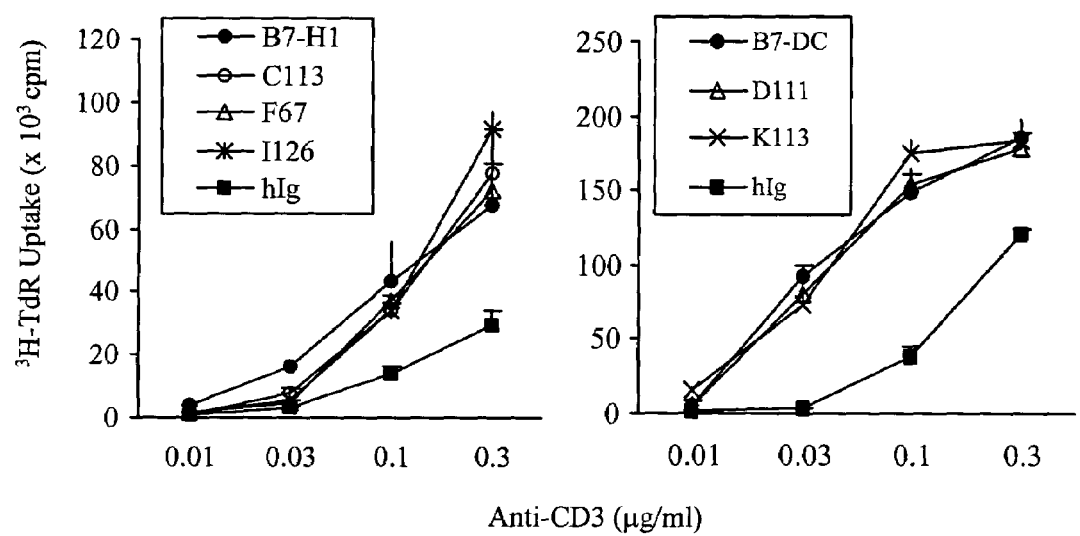
FIG. 12 is a pair of line graphs showing proliferation of PD-1$^{-/-}$ T cells after incubation with the indicated B7-H1 and B7-DC Ig fusion proteins in the presence of anti-CD3 mAb at the indicated concentrations. Human Ig was used as a negative control. Data depict one representative experiment of three.

Although B7-H1 and B-DC might costimulate T cell growth through a yet unknown receptor, these findings could be interpreted as an integrated stimulatory effect of unidentified costimulatory receptor(s) and PD-1. Therefore, the costimulatory effects of these mutants were tested in PD-1 deficient T cells. Wild type and variant B7-H1 polypeptides costimulated proliferation of PD-1$^{-/-}$ T cells as well as or better than PD-1$^{+/+}$ cells (FIG. 12 as compared with FIG. 11A). Similar results were obtained using wild type and variant B7-DC polypeptides. Thus, these observations strongly suggest that B7-H1 and B7-DC costimulate T cell growth through a non-PD-1 receptor.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

I claim:

1. A purified variant B7-H1 polypeptide which is a variant of a wild-type B7-H1 polypeptide, wherein said wild-type B7-H1 polypeptide binds to PD-1 and has the amino acid sequence set forth in SEQ ID NO:4, wherein said variant B7-H1 polypeptide comprises a substitution of the amino acid at position 67, 126, 37, 115, 124, 31, 49, 62, 98, or 129 of SEQ ID NO:4 and has binding affinity for PD-1 that is detectable by ELISA but is reduced by at least 50 percent as compared to the binding affinity of said wild-type B7H1 polypeptide for PD-1.

2. The purified variant B7-H1 polypeptide of claim 1, comprising a substitution of the amino acid at position 67 of SEQ ID NO:4.

3. The purified variant B7-H1 polypeptide of claim 2, wherein said substitution comprises replacing the amino acid at position 67 of SEQ ID NO:4 with an alanine residue.

4. The purified variant B7-H1 polypeptide of claim 1, comprising a substitution of the amino acid at position 126 of SEQ ID NO:4.

5. The purified variant B7-H1 polypeptide of claim 4, wherein said substitution comprises replacing the amino acid at position 126 of SEQ ID NO:4 with an alanine residue.

6. The purified variant B7-H1 polypeptide of claim 1, comprising a substitution of the amino acid at position 37 of SEQ ID NO:4.

7. The purified variant B7-H1 polypeptide of claim 6, wherein said substitution comprises replacing the amino acid at position 37 of SEQ ID NO:4 with a tyrosine residue.

8. The purified variant B7-H1 polypeptide of claim 1, comprising a substitution of the amino acid at position 115 of SEQ ID NO:4.

9. The purified variant B7-H1 polypeptide of claim 8, wherein said substitution comprises replacing the amino acid at position 115 of SEQ ID NO:4 with an alanine residue.

10. The purified variant B7-H1 polypeptide of claim 1, comprising a substitution of the amino acid at position 124 of SEQ ID NO:4.

11. The purified variant B7-H1 polypeptide of claim 10, wherein said substitution comprises replacing the amino acid at position 124 of SEQ ID NO:4 with a serine residue.

12. A polypeptide fragment of murine B7-H1 (SEQ ID NO:4) which comprises a variant at position 69 or 113 with respect to the sequence set forth in SEQ ID NO:4 and which inhibits binding of murine B7-H1 to murine PD-1, said polypeptide fragment comprising 259 to 271 amino acid residues and having Thr-290 of SEQ ID NO:4 at the carboxy terminal end.

13. A method of inhibiting the interaction between PD-1 and B7-H1, said method comprising contacting a PD-1 polypeptide with the polypeptide fragment of claim 12.

14. The method of claim 13, wherein said PD-1 is in vitro.

15. The method of claim 13, wherein said PD-1 is in a mammal.

16. The method of claim 15, wherein said method comprises administering the polypeptide fragment to the mammal.

17. The method of claim 15, wherein said mammal is a human.

18. The purified variant B7-H1 polypeptide of claim 1, comprising a substitution of the amino acid at position 31 of SEQ ID NO:4.

19. The purified variant B7-H1 polypeptide of claim 18, wherein said substitution comprises replacing the amino acid at position 31 of SEQ ID NO:4 with a serine residue.

20. The purified variant B7-H1 polypeptide of claim 1, comprising a substitution of the amino acid at position 49 of SEQ ID NO:4.

21. The purified variant B7-H1 polypeptide of claim 20, wherein said substitution comprises replacing the amino acid at position 49 of SEQ ID NO:4 with a serine residue.

22. The purified variant B7-H1 polypeptide of claim 1, comprising a substitution of the amino acid at position 62 of SEQ ID NO:4.

23. The purified variant B7-H1 polypeptide of claim 22, wherein said substitution comprises replacing the amino acid at position 62 of SEQ ID NO:4 with a serine residue.

24. The purified variant B7-H1 polypeptide of claim 1, comprising a substitution of the amino acid at position 98 of SEQ ID NO:4.

25. The purified variant B7-H1 polypeptide of claim 24, wherein said substitution comprises replacing the amino acid at position 98 of SEQ ID NO:4 with a phenylalanine residue.

26. The purified variant B7-H1 polypeptide of claim 1, comprising a substitution of the amino acid at position 129 of SEQ ID NO:4.

27. The purified variant B7-H1 polypeptide of claim 26, wherein said substitution comprises replacing the amino acid at position 129 of SEQ ID NO:4 with a serine residue.

* * * * *